(12) United States Patent
Watrous

(10) Patent No.: US 8,364,249 B2
(45) Date of Patent: Jan. 29, 2013

(54) AUTOMATIC GENERATION OF HEART SOUNDS AND MURMURS USING A LUMPED-PARAMETER RECIRCULATING PRESSURE-FLOW MODEL FOR THE LEFT HEART

(75) Inventor: Raymond L. Watrous, Belle Mead, NJ (US)

(73) Assignee: 3M Innovative Properties Company, St. Paul, MN (US)

( * ) Notice: Subject to any disclaimer, the term of this patent is extended or adjusted under 35 U.S.C. 154(b) by 1937 days.

(21) Appl. No.: 11/502,900

(22) Filed: Aug. 11, 2006

(65) Prior Publication Data

US 2008/0040087 A1 Feb. 14, 2008

(51) Int. Cl.
*A61B 5/04* (2006.01)
(52) U.S. Cl. ......... 600/513; 600/509; 600/514; 128/898
(58) Field of Classification Search .................. 600/509, 600/513, 514; 128/898
See application file for complete search history.

(56) References Cited

U.S. PATENT DOCUMENTS

| | | | | | |
|---|---|---|---|---|---|
| 3,137,092 | A | * | 6/1964 | Salerno | 600/28 |
| 3,384,981 | A | * | 5/1968 | Baessler et al. | 434/266 |
| 3,399,467 | A | * | 9/1968 | Ravin | 434/266 |
| 3,508,347 | A | * | 4/1970 | Keefer | 327/100 |
| 3,797,129 | A | * | 3/1974 | Ravin et al. | 434/266 |
| 3,947,974 | A | * | 4/1976 | Gordon et al. | 434/266 |
| 4,378,022 | A | * | 3/1983 | Suobank et al. | 600/528 |
| 5,337,752 | A | * | 8/1994 | Reeves | 600/513 |
| 5,769,641 | A | * | 6/1998 | Lampotang et al. | 434/272 |
| 6,220,866 | B1 | * | 4/2001 | Amend et al. | 434/266 |
| 6,273,728 | B1 | * | 8/2001 | van Meurs et al. | 434/268 |
| 6,527,558 | B1 | * | 3/2003 | Eggert et al. | 434/262 |
| 6,572,560 | B1 | * | 6/2003 | Watrous et al. | 600/528 |
| 6,629,937 | B2 | * | 10/2003 | Watrous | 600/586 |
| 6,953,436 | B2 | * | 10/2005 | Watrous et al. | 600/528 |
| 7,192,284 | B2 | * | 3/2007 | Eggert et al. | 434/268 |
| 7,300,407 | B2 | * | 11/2007 | Watrous | 600/528 |
| 7,510,398 | B1 | * | 3/2009 | Thornton | 434/262 |
| 2002/0052559 | A1 | * | 5/2002 | Watrous | 600/528 |
| 2003/0187362 | A1 | * | 10/2003 | Murphy et al. | 600/508 |
| 2004/0092846 | A1 | * | 5/2004 | Watrous | 600/586 |
| 2005/0048455 | A1 | * | 3/2005 | Hayamizu et al. | 434/262 |
| 2005/0222515 | A1 | * | 10/2005 | Polyshchuk et al. | 600/528 |
| 2008/0004508 | A1 | * | 1/2008 | Sun et al. | 600/300 |
| 2008/0013747 | A1 | * | 1/2008 | Tran | 381/67 |
| 2008/0138778 | A1 | * | 6/2008 | Eggert et al. | 434/262 |

(Continued)

OTHER PUBLICATIONS

Beyond Heart Sounds: An Interactive Teaching and Skills Testing Program for Cardiac Examination; SR Criley, DG Criley and JM Criley; Computers in Cardiology 2000, 27: 591-594.

(Continued)

*Primary Examiner* — Niketa Patel
*Assistant Examiner* — Christopher A Flory
(74) *Attorney, Agent, or Firm* — Kevin W. Weber

(57) ABSTRACT

Methods and systems for simulating a phonocardiogram (PCG) signal that includes an anomalous condition are provided. The method generates pressure and flow signals from a lumped-parameter heart model responsive to anomaly parameters. The anomaly parameters represent the anomalous condition. A timing profile or the timing profile and an amplitude profile are extracted from at least one of the generated pressure and flow signals. An anomalous signal is generated using the anomaly parameters and the extracted timing profile or timing profile and amplitude profile. The anomalous signal is time-aligned and combined with a predetermined non-anomalous signal to represent the PCG signal.

16 Claims, 16 Drawing Sheets

U.S. PATENT DOCUMENTS

2008/0138780 A1* 6/2008 Eggert et al. .......... 434/266
2008/0287819 A1* 11/2008 Gregson et al. .......... 600/528
2010/0304347 A1* 12/2010 Eggert et al. .......... 434/266

OTHER PUBLICATIONS

A Comparison of Faculty-Led Small Group Learning in Combination With Computer-Based Instruction Versus Computer-Based Instruction Alone on Identifying Simulated Pulmonary Sounds; Bernard M. Karnath M.D., Mandira Das Carlo, and Mark D. Holden; Dept. of Internal Medicine, Univ. of TX Medical Branch at Galveston, Galveston, TX USA; Teaching and Learning in Medicine, 16(1), 23-27. (2004).

http://nsr.bioeng.Washington.edu/Courses/BIOEN 589: Lab 3 Solution; BIOEN 589: Lab 3 Solution (Cardiac Mechanics). (2002).

www.cardionics.com/images/AuscConnpare.jpg; teaching software (screen shot) (2002).

www.cardionics.com/productdescriptions.htm; CardioSim Digital Heart Sound Teaching System (2002).

www.cardionics.com/productdescriptions.htm; Pocket Monitor Software for IPAQ (2002).

www.cardionics.com/productdescriptions.htm; Learning Cardiac Auscultation—CD-ROM (2002).

www.cardionics.com/pocketmonpics.htm; Pocket Monitor Pictures (2002).

www.cardionics.com/index.html; CardioSim VI, Digital Heart Sound Simulator (2002).

www.cardionics.com; S.A.M., The Student Auscultation Manikin for medical education (2002).

* cited by examiner

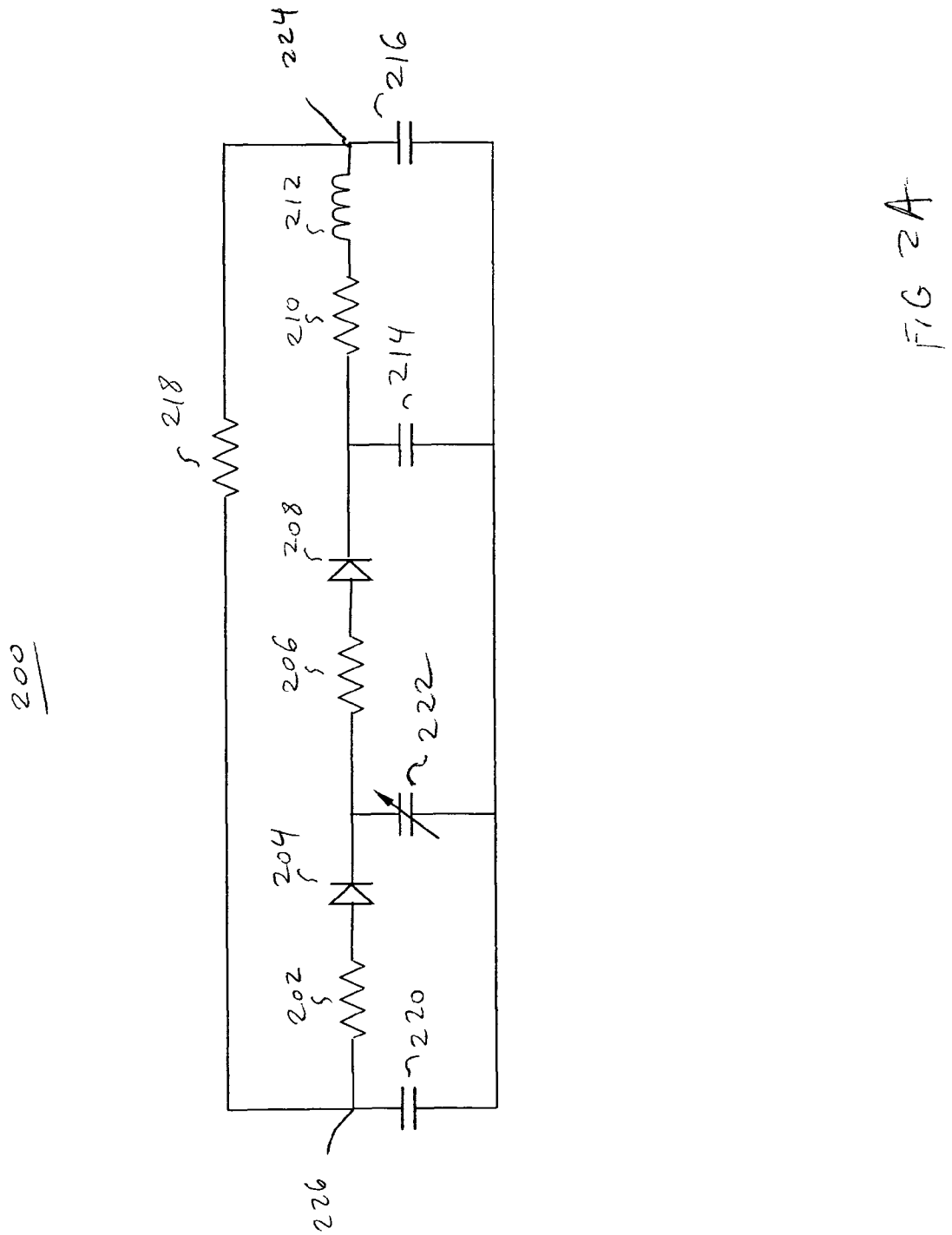

AUTOMATIC GENERATION OF HEART SOUNDS AND MURMURS USING A LUMPED-PARAMETER RECIRCULATING PRESSURE-FLOW MODEL FOR THE LEFT HEART

FIELD OF THE INVENTION

The present invention relates to auscultation training in general and, specifically, to systems and methods for simulating a phonocardiogram including an anomalous condition.

BACKGROUND OF THE INVENTION

Auscultation is typically used as a diagnosis tool in medicine, in particular for the diagnosis of cardiovascular disease. Auscultation relies on correctly determining which of the primary heart sounds correspond to the systolic phase of the heart and which sounds correspond to the diastolic phase of the heart. Learning auscultation may be difficult. The skill relies on detecting the correct sequence of brief events that occur close in time, a skill that is often difficult for human listeners. This is made more difficult when the systolic and diastolic intervals become more equal, such as typically occurs at elevated heart rates.

Auscultation training is available. For example, recordings of heart sounds, i.e. phonocardiograms (PCGs), that emphasis various pathological conditions exist. Many of these recordings are processed to emphasize particular features, such as enhancing a mid-systolic click to better distinguish the features of mitral valve prolapse. The recordings are also typically processed to reduce background noise commonly found in clinical practice, such that a physician new to clinical practice may have difficulty recognizing the distinguishing sounds in a clinical setting. Alternatively, training systems that use simulated heart sounds exist. Some of the simulated sounds, however, may seem unnatural to a trained physician or, as simulated, may not be physiologically feasible. Furthermore, teaching auscultation typically relies on memorization of heart sound patterns related to a particular pathophysiological condition. For example, memorizing the acoustical features of aortic stenosis.

Additionally, diagnostic instructional manuals rely on subjective descriptions of heart sounds, such as "musical" or "blowing" sounding murmurs, which require practice to appreciate. Furthermore, the practice and teaching of the clinical skill of auscultation of the heart has declined among physicians, partly due to a reliance on echocardiography testing. Recent studies have concluded that physicians can reliably identify only a small number of standard heart sounds and murmurs. Consequently, serious heart murmurs may go undetected by physicians.

SUMMARY OF THE INVENTION

The present invention is embodied in a method for simulating a phonocardiogram (PCG) signal that includes an anomalous condition. The method generates pressure and flow signals from a lumped-parameter heart model. The lumped-parameter heart model is responsive to anomaly parameters representing the anomalous condition. The method further extracts a timing profile or the timing profile and an amplitude profile associated with the anomalous condition from at least one of the generated pressure and flow signals. The method further generates an anomalous signal using the anomaly parameters and the extracted timing profile or the extracted timing profile and the extracted amplitude profile. The method further time-aligns and combines a predetermined non-anomalous signal and the generated anomalous signal to form a combined signal. The combined signal represents the PCG signal.

The present invention is further embodied in a method for teaching auscultation. The method presents hemodynamic parameters representing a plurality of anomalous conditions to a user. The method receives a selection from the user for one or more of the hemodynamic parameters representing one of the plurality of anomalous conditions. The method further applies the selected one or more hemodynamic parameters to a lumped-parameter heart model to generate pressure and flow signals representative of the anomalous condition. The method extracts a timing profile or the timing profile and an amplitude profile from the selected one or more hemodynamic parameters and at least one of the generated pressure and flow signals. The method further generates an anomalous phonocardiogram (PCG) signal from the extracted timing profile or the extracted timing profile and the extracted amplitude profile and presents the anomalous PCG signal to the user. The anomalous PCG signal is presented at least one of graphically and acoustically.

The present invention is further embodied in a system for simulating a phonocardiogram (PCG) signal representing an anomalous condition. The system includes a model parameter database for storing predetermined model parameters representative of the anomalous condition. The system further includes an input parameter selector for receiving hemodynamic parameters associated with the anomalous condition. The input parameter selector selects the predetermined model parameters associated with the received hemodynamic parameters from the model parameter database. The system further includes a lumped-parameter heart model circuit for generating pressure signals and flow signals responsive to the selected predetermined model condition parameters received from the input parameter selector. The system further includes an anomaly extractor for extracting a timing profile or the timing profile and an amplitude profile associated with the anomalous condition from at least one of the generated pressure signals and flow signals received from the lumped-parameter heart model circuit. The system further includes an anomalous signal generator for generating an anomalous signal using the selected predetermined model condition parameters and the extracted timing profile or the extracted timing profile and the extracted amplitude profile received from the anomaly extractor. The system further include a combiner for combining the anomalous signal received from the anomalous signal generator and a predetermined non-anomalous signal to form the PCG signal. The system also includes a display for displaying the PCG signal received from the combiner and an audio output terminal for providing an audio representation of the PCG signal.

The present invention is also embodied in a display for training auscultation. The display includes hemodynamic parameter selectors for selecting hemodynamic parameters associated with an anomalous condition. The display also includes a hemodynamic variable display for presenting hemodynamic variables associated with selected hemodynamic parameters selected from the hemodynamic parameter selectors. The display further includes heart sound variable selectors for selecting at least one of amplitude parameters and frequency characteristic parameters to adjust a synthesized anomalous phonocardiogram (PCG) signal. The display also includes a pressure graph and a flow graph generated by a lumped-parameter heart model responsive to the hemodynamic parameter selectors and the heart sound variable selectors. The display further includes a PCG signal indicator for displaying the synthesized anomalous PCG signal and an audio playback indicator for presenting an audio representation of the synthesized anomalous PCG signal.

The present invention is further embodied in a method for simulating a PCG signal. The method generates pressure and flow signals from a lumped-parameter heart model responsive to hemodynamic parameters. The method further extracts a timing profile or the timing profile and an amplitude profile associated with the hemodynamic parameters from at least one of the generated pressure and flow signals. The method simulates the PCG signal using the extracted timing profile or the extracted timing profile and the extracted amplitude profile.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 12 is an example display of the exemplary system shown in FIG. 1 that employs an embodiment of the present invention;

DETAILED DESCRIPTION OF THE INVENTION

Figure 1:
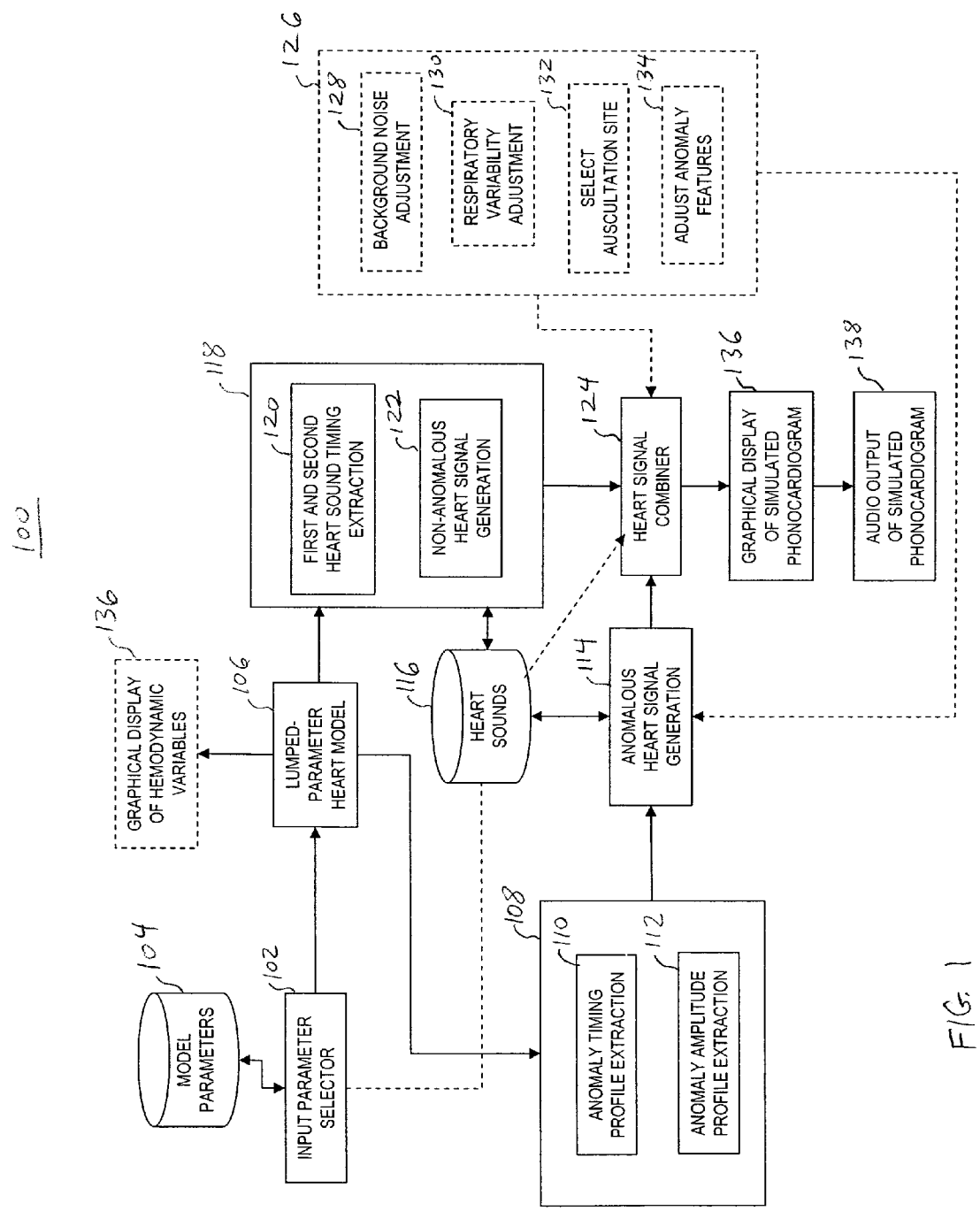
FIG. 1 is a functional block diagram illustrating an exemplary system for simulating a PCG signal representing an anomalous condition according to an aspect of the present invention.

Simulated auscultation training systems typically provide simulated phonocardiogram (PCG) signals associated with a particular anomalous condition, such as mitral regurgitation (MR). The first heart sound (S1), the second heart sound (S2) and other sounds can be inserted into a signal based upon a heart rate and known auscultation features. For example, MR includes auscultation features such as a dull or absent S1, a holosystolic murmur, a split S2, an exaggerated third heart sound (S3) and a short mid-diastolic rumble. Murmur frequency characteristics can be simulated from measured frequency characteristics of MR. A simulated signal can thus use these parameters to construct a signal representing MR, for example, by inserting recorded S1, S2 and murmur events at expected onset times at a predetermined heart rate. However, these parameters are related to auscultatory features, and may not be grounded in a physiological understanding of the hemodynamic parameters of the heart.

The hemodynamics of the heart are the underlying mechanism for generating S1, S2 and S3 that are associated with valve closure, murmurs related to turbulent flow of blood through the heart and other sounds such as ejection sounds (ESs), opening snaps (OSs) and midsystolic clicks.

In simulating the various pathological conditions based on auscultatory features alone, a simulated PCG signal for one heart rate may not appear realistic at another heart rate. If heart sound events are merely inserted into a signal corresponding to a faster heart rate, there is no accounting for any physiological pressure and flow changes that may occur and affect behavior, such as S1 and S2 loudness or respective systole and diastole durations. Furthermore, model parameters used to simulate PCG signals may not represent physiologically correct hemodynamic behavior. Accordingly, sounds generated in this manner may be unnatural and, thus, of little educational value.

The present invention generates anomalies and representative heart sounds based on an electrical analog model of the hemodynamics of the heart. A lumped parameter pressure-flow model of the heart is used to generate pressure and flow signals associated with various portion of the heart that are representative of the corresponding hemodynamics. The lumped-parameter model is desirably provided with input parameters such as a heart rate and physiological parameters associated with an anomaly condition that affect the electrical model of the heart. At least a timing profile is determined from the generated pressure and/or flow signals to develop a signal representative of the anomaly. An amplitude profile may additionally be determined and used to develop the signal representative of the anomaly. The simulated PCG signal is thus generated relative to the electrical analog model. The present invention may provide insight into how heart sounds are generated. The present invention may thus provide an auscultation training system emphasizing the physiological processes that underlie heart sound generation.

FIG. 1 is a functional block diagram of an exemplary system 100 for simulating a PCG signal representing an anomalous condition according to the present invention. Exemplary system 100 includes a model parameters database 104 for storing model parameters associated with various anomalous conditions. Input parameter selector 102 may receive hemodynamic parameters (not shown) associated with an anomalous condition. It is understood that the received hemodynamic parameters may not be the same as the model input parameters that are associated with an anomalous condition. Input parameter selector 102 may thus translate the received hemodynamic parameters to appropriate model parameters for an anomalous condition and retrieve the appropriate model parameters from model database 104.

It is understood that the received hemodynamic parameters may also represent a non-anomalous condition consisting of only S1 and S2 events. The non-anomalous condition may further model types of arrhythmias. For a non-anomalous condition, input parameter selector 102 may translate the received hemodynamic parameters to appropriate non-anomalous model parameters and retrieve the appropriate model parameters from model database 104.

The anomalous condition may be associated with one or more of a functional murmur, a valvular pathology, systemic hypertension and a congenital anomaly. Types of valvular anomalies may include regurgitation, stenosis and prolapse, or any combination thereof. It is understood that any desired anomalous condition may be simulated using an appropriate lumped-parameter heart model.

Hemodynamic parameters may include one or more parameters such as a constant heart rate, a variable heart rate, a respiration rate, a pathophysiology, a sinus arrhythmia parameter, an electrophysiology parameter, and a premature ventricular beat parameter. A pathophysiology may represent any anomalous condition, for example, mitral valve prolapse. A variable heart rate parameter may be used to model arrhythmias. A sinus arrhythmia parameter may be used to illustrate arrhythmia variation with respiration. An electrophysiology parameter may be used to represent various electrophysiological conditions, such as to model timing of a left bundle branch block or to represent murmurs that also rely on electrophysiology information. It is understood that other desired hemodynamic parameters may be included within the scope of the present invention.

Lumped-parameter heart model circuit 106 receives the model parameters from input parameter selector 102 and generates pressure and flow signals from an electrical analog model of the heart. Lumped-parameter heart model circuit 106 may include several electrical analog models of the heart. The received hemodynamic parameters may further include a selection of a type of electrical analog model to use for generating pressure and flow signals.

Hemodynamic variables may be computed by lumped-parameter heart model circuit 106 and provided to graphical display 136 based on the received hemodynamic parameters. Hemodynamic variables may include one or more known in the art variables such as a stroke volume, an end-diastolic volume, a cardiac output, an ejection fraction, a systolic/diastolic blood pressure, a mean arterial pressure, an estimated mean arterial pressure, a systolic interval duration, and a diastolic interval duration. Alternatively, the hemodynamic variables may be computed by input parameter selector 102.

Anomaly extractor circuit 108 receives the computed pressure and flow signals from lumped-parameter heart model circuit 106 and extracts at least a timing profile from the pressure and flow signals. Depending upon the anomalous condition, anomalous extractor circuit 108 may perform timing profile extraction using anomaly timing profile extraction circuit 110 if the anomaly includes only anomaly events, or may further include anomaly amplitude profile extraction circuit 112, if the anomaly includes one or more types of murmurs. An anomaly event may include one or more of an OS, an ES, an S3, a fourth heart sound (S4) and/or a click. An S3 may represent an anomalous event, for example if an S3 is present in an adult PCG.

An anomaly may be represented by one ore more types of murmurs located in systole, diastole and any combination thereof. Each murmur has a corresponding murmur frequency characteristic, and a murmur amplitude profile. For example, an anomalous condition such as aortic regurgitation may include an early-mid systolic flow murmur having a first frequency characteristic and a decrescendo diastolic murmur having a further frequency characteristic.

Heart sounds database 116 may include predetermined S1, S2, S3, ES, OS and click sounds as well as predetermined signals with which to generate anomalous and non-anomalous signals.

Anomalous heart signal generation circuit 114 may receive the extracted timing profile from anomaly extraction circuit 108 and may further receive the extracted amplitude profile to generate an anomalous signal based on the selected model condition parameters (connection to input parameters selector 102 not shown) and a predetermined signal from heart sounds database 116. The timing and amplitude profiles may be used to form one or more types of murmurs in the anomalous signal. Anomalous heart signal generation circuit 114 may retrieve one or more anomalous events from heart sounds database 116 and insert them into the predetermined signal at appropriate onset times based on results from anomaly extraction circuit 108.

Non-anomalous signal circuit 118 may receive pressure signals from lumped-parameter heart model circuit 106 and generate a non-anomalous signal. The non-anomalous signal desirably includes S1 and S2 events. Non-anomalous signal circuit 118 may include S1 and S2 timing extraction circuit 120 which determines S1 and S2 onset times, respectively, from the received pressure signals.

Non-anomalous signal circuit 118 may also include non-anomalous heart signal generation circuit 122 which generates the non-anomalous signal using predetermined S1 and S2 events and a predetermined signal, received from heart sounds database 116. Non-anomalous heart signal generation circuit 122 desirably inserts the S1 and S2 events into the signal using the extracted onset times from S1 and S2 timing extraction circuit 120.

In an alternative embodiment, heart sounds database 116 may include a predetermined number of non-anomalous signals that are associated with predetermined model parameters. Input parameter selector 102 may retrieve a non-anomalous signal from heart sounds database 116 based on the selected model parameters and transmit the non-anomalous signal to heart signal combiner 124, as indicated by the dashed lines.

Heart signal combiner 124 desirably combines the anomalous signal retrieved from anomalous heart signal generation circuit 114 and a non-anomalous signal retrieved from non-anomalous signal circuit 118 or, alternatively, a predetermined non-anomalous signal. The combined signal forms the PCG signal. The PCG signal includes S1 and S2 events and may further include one or more of a click, one or more types of murmurs, an OS, an ES and an S3 event.

Exemplary system 100 may further include a heart signal adjustor circuit 126 for adjusting one or more characteristics of the PCG signal. Heart signal adjustor circuit 126 may receive adjustment parameters from a user (not shown). Heart signal adjustor circuit 126 may include a background noise adjustment circuit 128 coupled to heart signal combiner 124 which may vary the background noise of the PCG signal.

Heart signal adjustor circuit 126 may further include a respiratory variability adjustment circuit 130 coupled to heart signal combiner 124 to vary an amount of a respiration effect on the PCG signal.

Heart signal adjustor circuit 126 may also include an auscultation site selector circuit 132. Auscultation site selector circuit 132 may be coupled to heart signal combiner 124 and may adjust the various heart sounds in the PCG signal, for example a murmur loudness or the presence of a midsystolic click, according to known auscultatory features for the selected auscultation site and anomalous condition.

Heart signal adjustor circuit 126 may further include an anomaly feature adjustment circuit 134 coupled to anomalous heart signal generation circuit 114 for adjusting the loudness of an anomaly, i.e. a murmur loudness, and/or a frequency characteristic of the anomaly. For example, the bandwidth of a murmur may be adjusted and the loudness of the murmur may also be adjusted according to a selected murmur grade. It is understood that heart signal adjustor circuit 126 may also be coupled to non-anomalous signal circuit 118.

The PCG signal provided by heart signal combiner circuit 124 is desirably provided to graphical display 136. The PCG signal may be provided by heart signal combiner circuit 124 to an audio output port 138 for reviewing the audio signal. The audio output port 138 may be coupled to, for example, headphones or a loudspeaker.

Although model parameters database 104 and heart sounds database 116 are illustrated as separate databases, it is understood that these databases may be one database.

In an exemplary embodiment, a graphical user interface (GUI) is provided for selecting hemodynamic parameters and hemodynamic variables and to display the resulting PCG signal. A user may select hemodynamic parameters, for example, by using a keyboard, a computer mouse, a touch screen, or any combination thereof. It is contemplated that components of exemplary system 100 may be provided in computer program software and may be performed on any suitable computer.

FIG. 2A shows a circuit diagram 200 of a lumped parameter pressure-flow model of the left heart. The model represents the left side of the heart, including the mitral valves and aortic valves. The mitral and aortic valves are represented as diodes 204 and 208, respectively. The mitral valve also includes a resistance $R_{mit}$ 202. Similarly, the aortic valve includes a resistance $R_{av}$ 206.

Figure 2B:
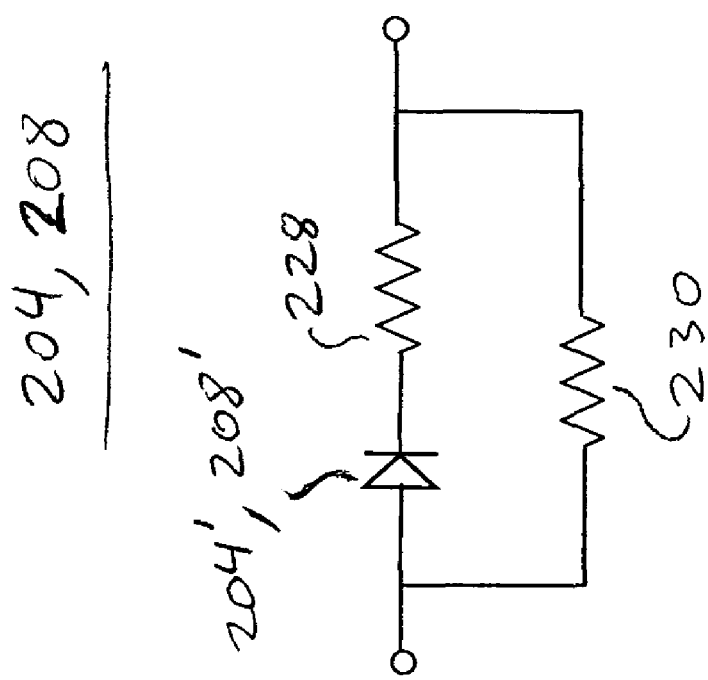
FIG. 2B (Prior Art) is a circuit diagram illustrating a diode model of a heart valve including a forward and backward resistance.

Each of diodes 204 and 208 may be further modeled as illustrated in FIG. 2B. In this figure, resistance 228 represents a forward resistance and resistance 230 represents a backward resistance of diodes 204' and/or 208', to represent stenosis and regurgitation effects, respectively. Diodes 204, and 208' are the same as diodes 204 and 208 except that diodes 204 and 208 may include a forward resistance 228 and/or a backward resistance 230.

The aortic system is represented by a resistance $R_{aor}$ 210, an inductance $L_{aor}$ 212, and a capacitance $C_{aor}$ 214. The arterial system is represented by a capacitance $C_{art}$ 216. The venous system is represented by a capacitance $C_v$ 220. A feedback pathway from the aortic section to the mitral valve is represented by a systemic resistance $R_{sys}$ 218, between the aortic output node 224 and atrial input node 226. The feedback pathway desirably encompasses the pulmonary circulation in the systemic elements. A variable compliance $C_{LV}$ 222 represents the contraction and relaxation of the left ventricle (LV).

It is understood that other left-side heart models may be used. The left-side heart model may include more complex impedance relationships, such as between the aortic output node 224 and the atrial input node 226. The model may further include relationships between the propagation of sounds from the heart valves or points of origin to the chest surface. Although not illustrated, it is contemplated that a four-chamber heart model may be used. A four-chamber heart model may provide simulation of further types of murmurs not capable of being modeled by a left-side heart model, as well as further simulation of, for example, the S4 heart sound and splitting of the S1 and/or S2 heart sounds.

It is contemplated that the lumped-parameter pressure heart circuit represented by circuit diagram 200 may be performed by a simulated circuit or an actual circuit or any combination thereof.

Figure 2C:
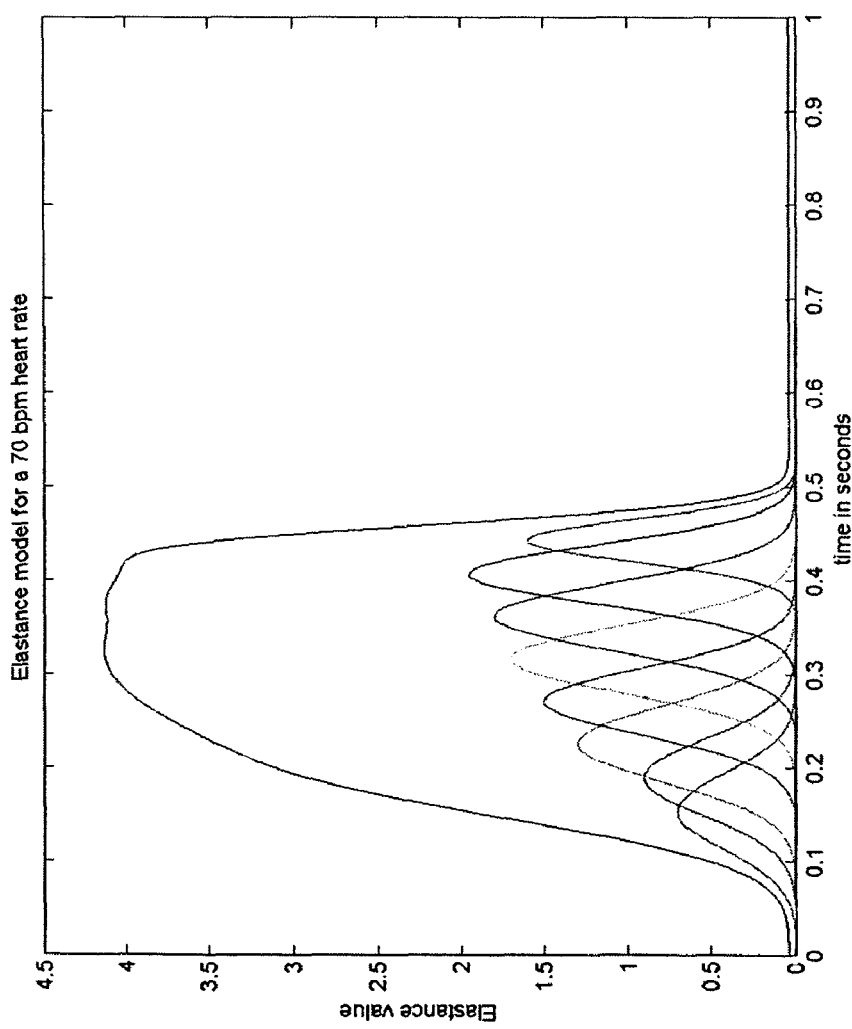
FIG. 2C (Prior Art) is a variable elastance model for use with the lumped-parameter pressure-flow model of FIG. 2A.

In an exemplary embodiment, variable compliance 222 is represented by a sum of exponentials variable elastance model, as shown in FIG. 2C. It is contemplated that a clipped-sinusoidal compliance model may also be used. The elastance model is desirably heart-rate dependent, and thus the heart-rate of the system can be varied such that it increases or decreases the variable compliance 222.

Adjusting variable compliance 222 adjusts the systolic pressure, the duration of contraction, and thus the systolic interval.

The lumped-parameter model circuit 200 may be represented by second-order differential equations as:

$$\frac{dP_{lv}}{dt} = P_{lv} \cdot \frac{dE_{last}}{dt} \cdot \frac{1}{E_{last}} + \left(I_{mit} - I_{av} - \frac{dV_{lvr}}{dt}\right) \cdot E_{last}, \quad (1)$$

$$R_{mit}\frac{dI_{mit}}{dt} = \frac{I_{sys} - I_{mit}}{C_v} - \frac{dP_{lv}}{dt}, \quad (2)$$

$$R_{av}\frac{dI_{av}}{dt} = \frac{dP_{lv}}{dt} + \frac{I_{aor} - I_{av}}{C_{aor}}, \quad (3)$$

$$R_{sys}\frac{dI_{sys}}{dt} = \frac{I_{aor} - I_{sys}}{C_{art}} - \frac{I_{sys} - I_{mit}}{C_v}, \quad (4)$$

and $$L_{aor}\frac{dI_{aor}}{dt} = -(R_{aor} \cdot I_{aor} + R_{av} \cdot I_{av} + R_{mit} \cdot I_{mit} + R_{sys} \cdot I_{sys}), \quad (5)$$

where $$E_{last} = \frac{1}{C_{lv}}. \quad (6)$$

Equations 1-6 may be solved for pressure and flow signals. Pressure signals $P_{lv}$, $P_{aor}$ and $P_v$ represent the left ventricular (LV), aortic and venous pressures, respectively. Flow signals $I_{av}$, $I_{aor}$, $I_{mit}$, $I_{sys}$ represent flow through the aortic valve, the aortic portion, the mitral valve and the systemic portion of the circuit, respectively. $V_{lvr}$ represents a relaxation volume of the LV.

Table 1 represents parameter values according to for an exemplary embodiment of the present invention. The parameter values are desirably based upon known-in-the-art hemodynamic values of the heart. It is understood that these values may be varied, for example, based on the age of the patient. The present invention may further also be applied to veterinarian training, and as such the model and parameter values may represent various animal heart hemodynamics.

TABLE 1

| | |
|---|---|
| $R_{aor}$ | 0.2 mmHg * s/ml |
| $R_{sys}$ | 1.05 mmHg * s/ml |
| $C_{aor}$ | 0.7-1.1 ml/mmHg |

TABLE 1-continued

| | |
|---|---|
| $C_v$ | 10 ml/mmHg |
| $C_{art}$ | 1.6 ml/mmHg |
| $L_{aor}$ | 0.5 g/cm$^4$ (or equivalently 0.000375 mmHg * s$^2$/ml) |
| Forward $R_{mit}$ | 0.025 mmHg * s/ml |
| Backward $R_{mit}$ | 10$^2$ mmHg * s/ml |
| Forward $R_{av}$ | 0.005 mmHg * s/ml |
| Backward $R_{av}$ | 10$^2$ mmHg * s/ml |
| $V_{lv}$ at diastole | 30 ml |
| $V_{lv}$ at systole | 10 ml |
| $C_{LV}(t)$ | 0.04-4.6 ml/mmHg |

Equations 1-6 may be solved, for example, using an ordinary differential equation (ODE) solver. In an exemplary embodiment, MATLAB® ODE solver is used to generate pressure and flow signals from equations 1-6. Initial conditions for the solution may be chosen based on considerations of time alignment of the variable elastance model with circuit 200. As described in more detail below, the generated pressure and flow signals may be used to determine anomalous and non-anomalous signals to represent an anomalous condition.

Arrhythmias may be modeled by varying the heart rate and through the variable compliance 222. Variations in the heart rate and modeling of various arrhythmias may modify the associated pressure-flow relationships, which may have the expected effect on valve opening and closure timing. Sinus arrhythmias may be simulated by adjusting an instantaneous heart rate relative to a respiration rate. Adjusting the instantaneous heart rate relative to the respiration rate has the expected effect on the systolic interval through variable compliance 222 of increasing the instantaneous heart rate with inspiration.

Premature contractions, which typically include incomplete ventricular filling, may be introduced into circuit 200 to model post-ventricular lengthening, which is often observed with ectopic premature beats. Variations in the heart rate and modeling of various arrhythmias may modify associated pressure-flow relationships which may have an expected effect on valve opening and closure timing.

Various pathological conditions can be modeled by changing the parameters of circuit 200, as described in more detail below. Circuit 200 allows for changes in the pressure-flow relationships to have expected physiological effects on timing of systole and diastole. For example, aortic stenosis modeling parameters will increase LV pressure and delay the onset of diastole, thus lengthening the systolic interval. Systemic hypertension may be modeled by increasing the value of resistance 218. Increasing resistance 218 may provide a higher back pressure across the aortic valve, diode 208, and may thus cause a louder S2 sound, which is an expected finding in hypertension.

Figure 3:
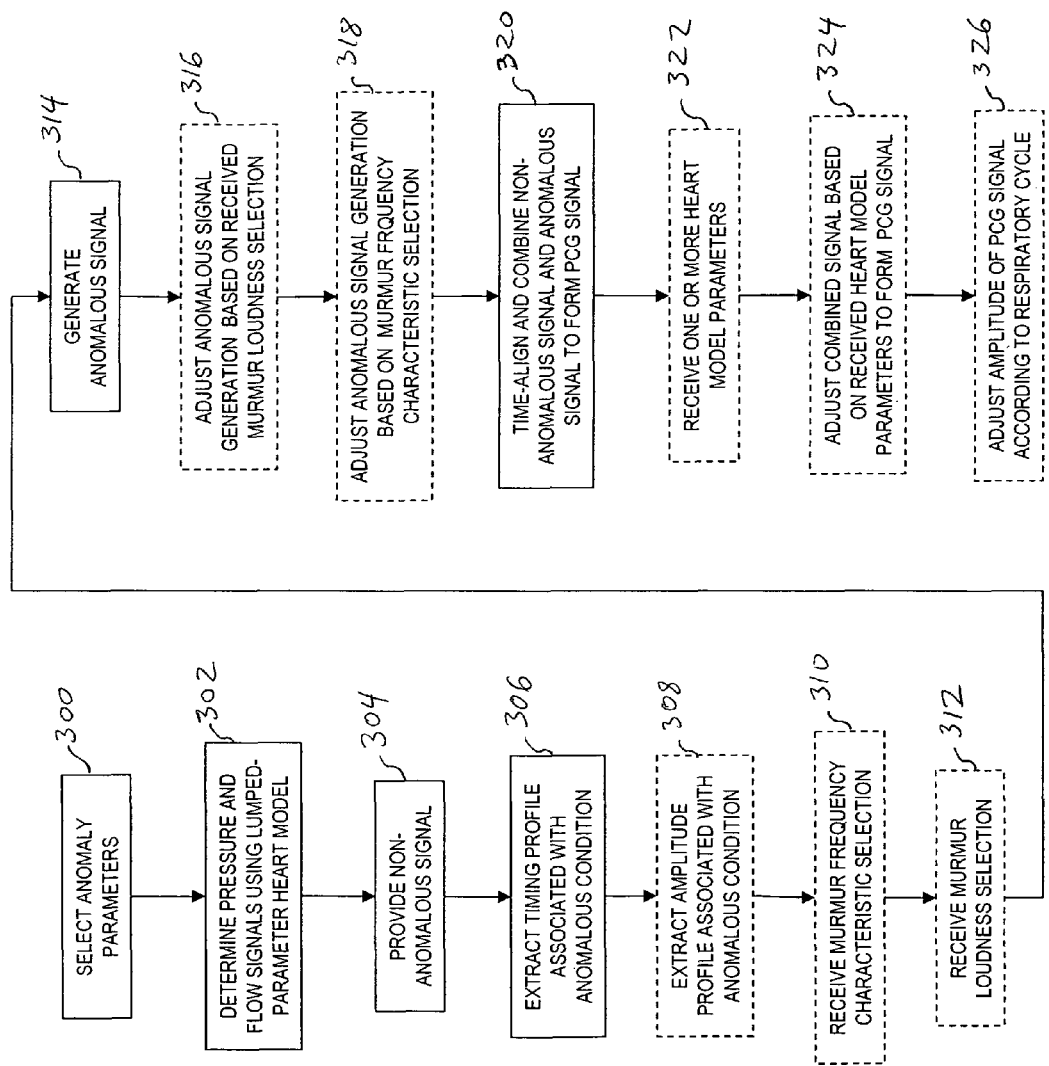
FIG. 3 is a flowchart illustrating an exemplary method for simulating a PCG signal including an anomalous condition according to an aspect of the present invention.
Figure 2:
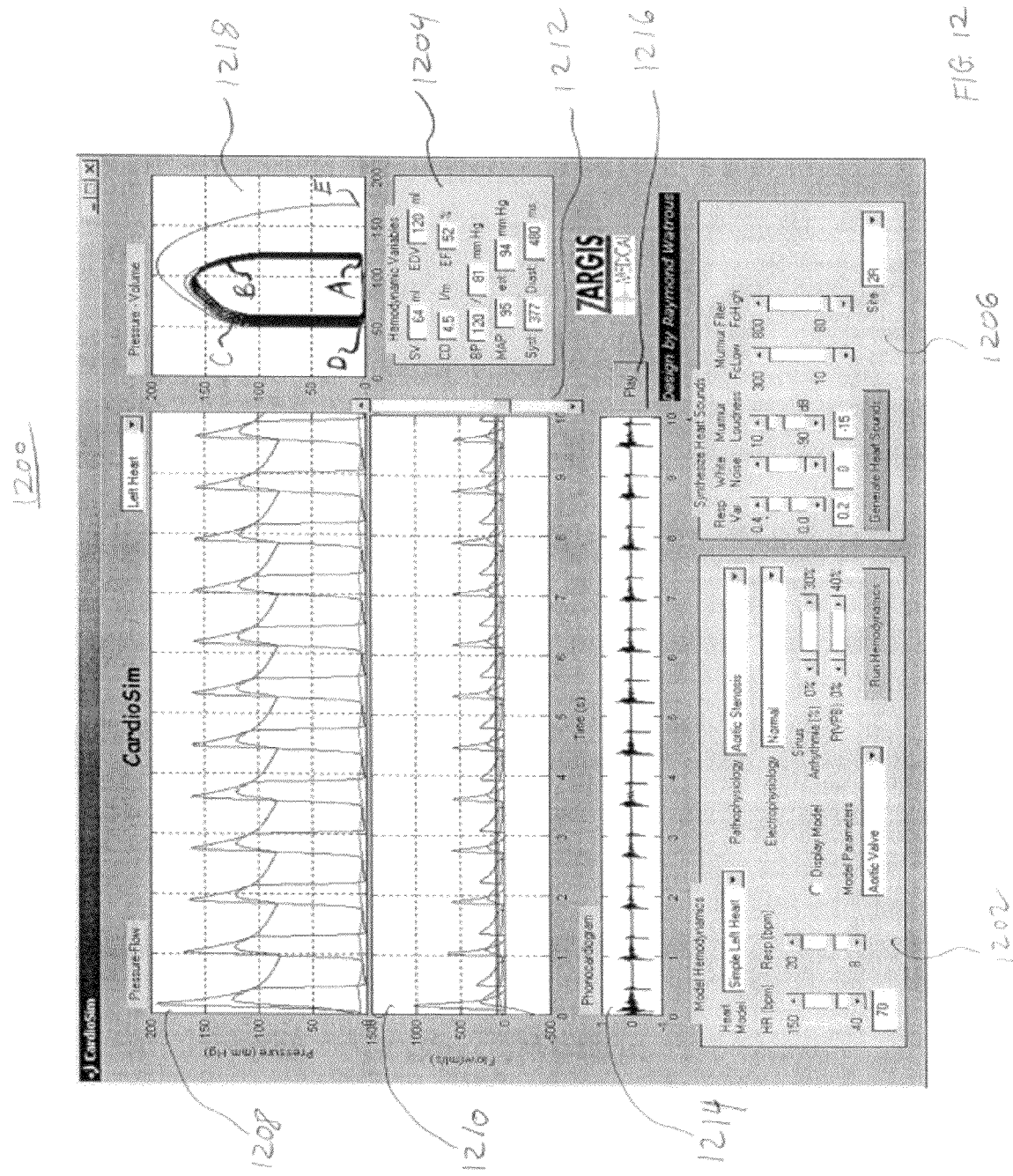
FIG. 2A (Prior Art) is a circuit diagram illustrating a lumped-parameter pressure-flow model of the left heart.

FIG. 3 shows a flowchart illustrating an exemplary method for simulating a PCG signal that includes an anomalous condition according to the present invention. In step 300, anomaly parameters are selected. The anomaly parameters may correspond to parameters selected from model parameter database 104 by input parameter selector 102 (FIG. 1). In step 302, pressure and flow signals are determined using a lumped-parameter heart model, such as circuit 200 (FIG. 2), described above.

In step 304, a non-anomalous signal is provided. The non-anomalous signal may be generated, for example using non-anomalous circuit 118 (FIG. 1), or it may be retrieved from a database such as heart sounds database 116, based on the received hemodynamic parameters (FIG. 1).

In step 306, a timing profile associated with the anomalous condition is extracted, for example using anomaly timing profile extraction circuit 110 (FIG. 1). In alternate step 308, an amplitude profile associated with the anomalous condition is extracted, such as with anomaly amplitude profile extraction circuit 112 (FIG. 1). For example, if the anomalous signal includes a murmur, an amplitude profile may be extracted to determine an amplitude profile of the murmur.

In alternate step 310, a murmur frequency characteristic selection is received, for example, by anomaly features adjustment circuit 134 (FIG. 1). In further alternate step 312, a murmur loudness selection is received, such as from anomaly features adjustment circuit 134. It is contemplated that alternate steps 310 and 312 may be performed in any order or concurrently.

In step 314, an anomalous signal is generated, for example using anomalous heart signal generation circuit 114 (FIG. 1) and based upon step 306 or additionally based on one or more of alternate steps 308, 310 and 312.

In alternate step 316, if alternate step 312 is performed, the anomalous signal, i.e. a murmur, is adjusted based on the received murmur loudness selection. The murmur loudness selection may further be related to a murmur grade such that the murmur loudness may be adjusted relative to a murmur grade. In alternate step 320, if alternate step 310 is performed, the anomalous signal, i.e. a murmur, may be adjusted based on the received murmur frequency characteristic selection. It is contemplated that alternate steps 316 and 318 may be performed in any order or concurrently.

In step 320, the non-anomalous and anomalous signals are time-aligned and combined, for example using heart signal combiner circuit 124 (FIG. 1), to form a combined signal that represents the PCG signal including the anomalous condition. In alternate step 322, one or more heart model parameters, such as from heart signal adjustor circuit 126 may be received. The heart model parameters may include one or more of a background noise level, an auscultation site and a respiration variability. It is understood that other heart model parameters that may adjust the PCG signal according to desired characteristics may be included. In alternate step 324, the combined signal may be adjusted based on the received heart model parameters to form the PCG signal. The PCG signal may be displayed, for example with graphical display 136 and may also be presented as an audio signal, such as with headphones coupled to audio output 138.

In alternate step 326, the amplitude of the PCG signal may be adjusted according to a selected respiratory cycle. The respiratory cycle may be one of the anomaly parameters selected by input parameter selector (102). In an exemplary embodiment, the respiratory cycle is represented by a sinusoidal signal have a period associated with a selected respiratory rate. The respiration cycle may be used to modify the amplitude of the PCG signal according to a selectable gain factor. The respiratory cycle may simulate an interposition of an air volume between the heart and an auscultation sensor during respiration, such that PCG signal amplitude decreases with inspiration.

It is contemplated that the PCG signal may be formed from only the non-anomalous signal. For example, a physician may examine variations in S1 and S2 sounds with various arrhythmias. As another example, a physician may examine variations in S and S2 sounds as the heart rate is increased in a non-anomalous signal having a constant heart rate.

Figure 4:
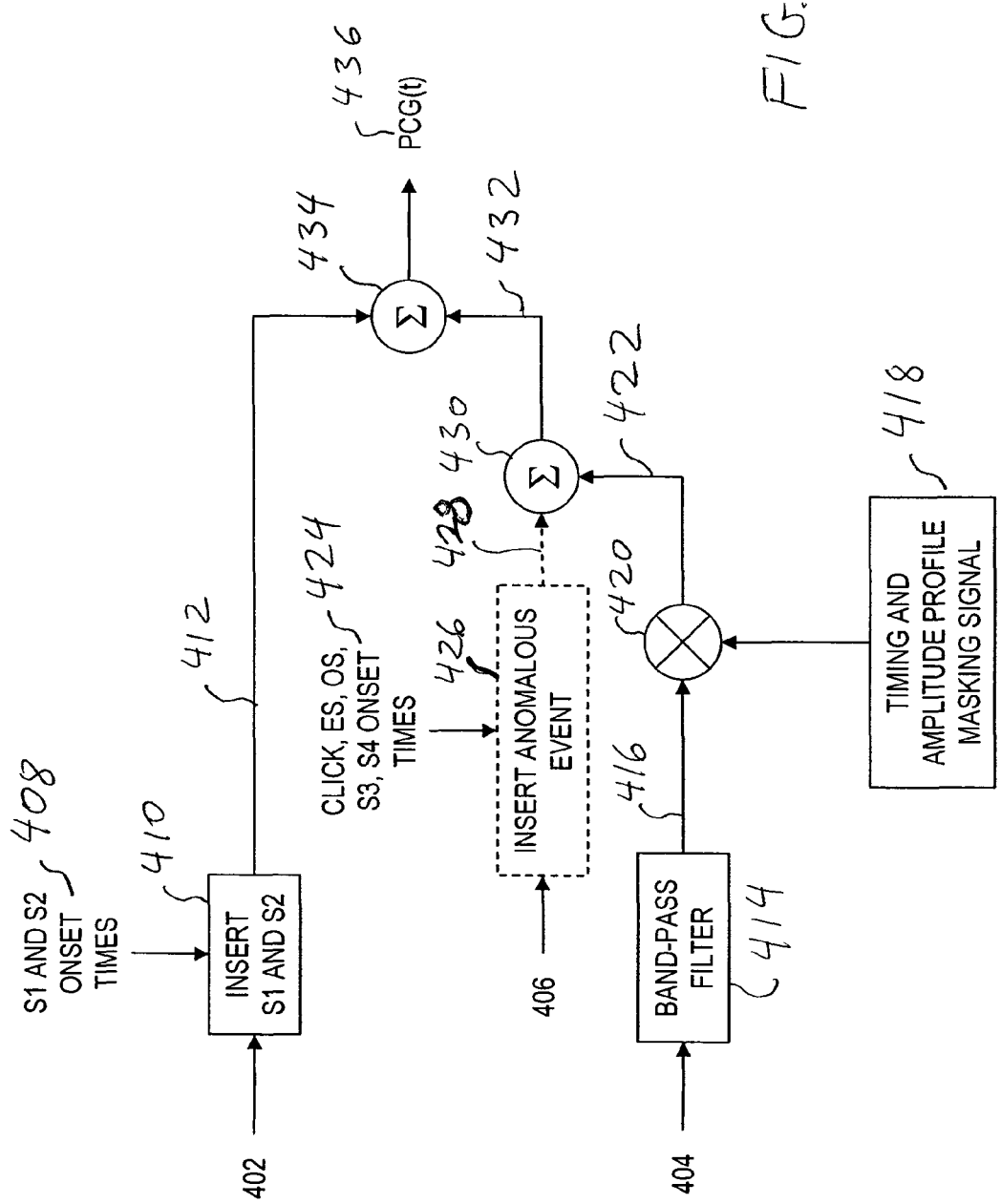
FIG. 4 is a functional block diagram illustrating an exemplary method for combining a non-anomalous signal and an anomalous signal according to an aspect of the present invention.

FIG. 4 shows a functional block diagram illustrating an exemplary method for combining a non-anomalous signal and an anomalous signal according to an embodiment of the present invention. Signal 402 represents a predetermined signal upon which to generate non-anomalous signal 412. Signal 404 represents a predetermined signal upon which to generate anomalous signal 422 consisting of murmurs. Signal 406 represents a predetermined signal upon which to generate anomalous event signal 428, such as a signal consisting of one or more OS, ES, click, S3 and S4 heart sounds.

Although PCG signal 436 is shown as the summation of signals 412 and 432 by summer 434, it is understood that PCG signal 436 may include only non-anomalous signal 412. Signal 432 may include only anomalous signal 422. Alternatively, signal 432 may include the combination of anomalous signal 422 and anomalous event signal 428 combined by summer 430. Alternatively, signal 432 may only consist of anomalous event signal 428. The combination of non-anomalous signal 412 and signal 432 is desirably based on the selected anomaly parameters.

Non-anomalous signal 412 may be generated using predetermined signal 402. In an exemplary embodiment, signal 402 is a signal of zeros having a predetermined length. The predetermined length may be determined relative to generating a predetermined number of heart cycles for each heart rate. Alternatively, the predetermined length may be a fixed length. The fixed length may be a function of a predetermined sampling rate for playback of the generated PCG signal 436, for example with audio output circuit 138 (FIG. 1). The fixed length may also be determined relative to a predetermined number of heart cycles associated with a predetermined lowest heart rate. In this manner, a simulated signal with the lowest heart rate may present at least one full cycle, systole and diastole, of a heart beat.

S1 and S2 onset times 408 are provided to insertion block 410, for example using non-anomalous heart signal generation circuit 122 (FIG. 1) to insert predetermined S1 and S2 events, retrieved from a database, into signal 402 at the appropriate onset times. Onset times 408 may be determined, for example by S1 and S2 timing extraction circuit 120 (FIG. 1), and as described below. The predetermined S1 and S2 events may be retrieved from a database such as heart sounds database 116 (FIG. 1).

In an alternate embodiment, signal 402 may represent a non-anomalous signal selected from a database, such as heart sounds database 116 (FIG. 1), according to selected anomaly parameters. In this alternate embodiment, insertion block 410 is not required and signal 412 is the same as signal 402.

Anomalous signal 422 may be generated using predetermined signal 404. In an exemplary embodiment, signal 404 is a white noise signal having a length equal to signal 402. A band-pass filter 414 is applied to signal 404 to generate filtered noise signal 416. Band-pass filter 414 desirably includes frequency characteristics associated with the selected anomaly parameters. The frequency characteristics may be determined based on descriptions and published PCGs of anomalous conditions.

Alternatively, frequency characteristics of recorded murmurs may be autoregressively (AR) modeled. Murmurs may then be synthesized using the AR modeling coefficients to generate more natural sounding murmurs in terms of synthesized frequency characteristics. In a further alternate embodiment, a pressure difference may be used to generate the frequency characteristics of the murmur. A transvalvular pressure may be mapped onto an instantaneous frequency to synthesize a murmur having a time-varying frequency that is proportional to the transvalvular pressure. Respiration may also be used in conjunction with the filling of ventricles and may thus affect the timing of the murmur. The amplitude profile of the murmur may still be determined by the masking signal 418, described below.

A timing and amplitude profile masking signal 418 is desirably combined with filtered noise signal 416 by combiner 420 to form anomalous signal 422. Timing and amplitude profile masking signal 418 may be determined, for example from anomaly timing profile extraction circuit 110 and anomaly amplitude profile extraction circuit 112 (FIG. 1) and is further described below. Although combiner 420 is illustrated as being a multiplier, it is contemplated that timing and amplitude profile masking signal 416 may be combined by any combining means, for example, using multiplication, or using a logical AND function.

Anomalous event signal 428 may be generated using predetermined signal 406. Signal 406 may be the same as signal 402 or may be non-anomalous signal 412, i.e. after non-anomalous events are inserted into signal 402. In an exemplary embodiment, signal 406 is the non-anomalous signal 412. One or more onset times 424 for an event such as a click(s), an ES, an OS, an S3 and an S4 are provided to insertion block 426 to insert one or more predetermined anomalous events into signal 406 at the appropriate onset times to form anomalous event signal 428, as described below. Insertion block 426 may be anomaly timing profile extraction circuit 110 (FIG. 1). The predetermined anomalous events may be retrieved, for example from heart sounds database 116 (FIG. 1).

Figure 5:
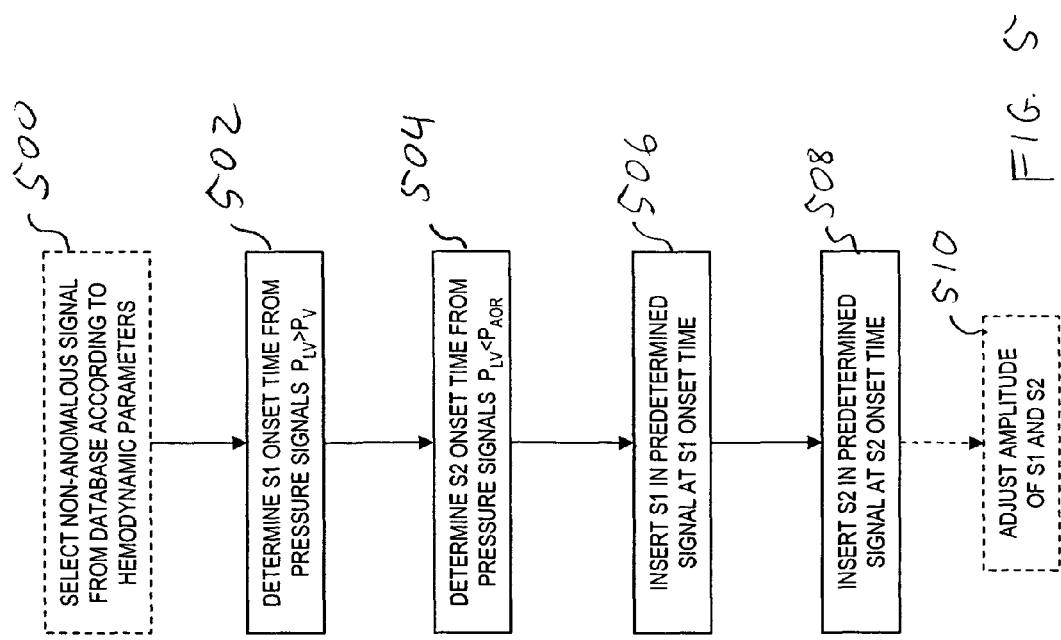
FIG. 5 is a flowchart illustrating an exemplary method for generating a non-anomalous signal according to an aspect of the present invention.

FIG. 5 shows a flowchart illustrating an exemplary method for generating a non-anomalous signal according to the present invention. In alternate step 500, a non-anomalous signal is selected from a database, such as heart sounds database 116 (FIG. 1), according to the received hemodynamic parameters and the process for generating a non-anomalous signal is complete.

Figure 6:
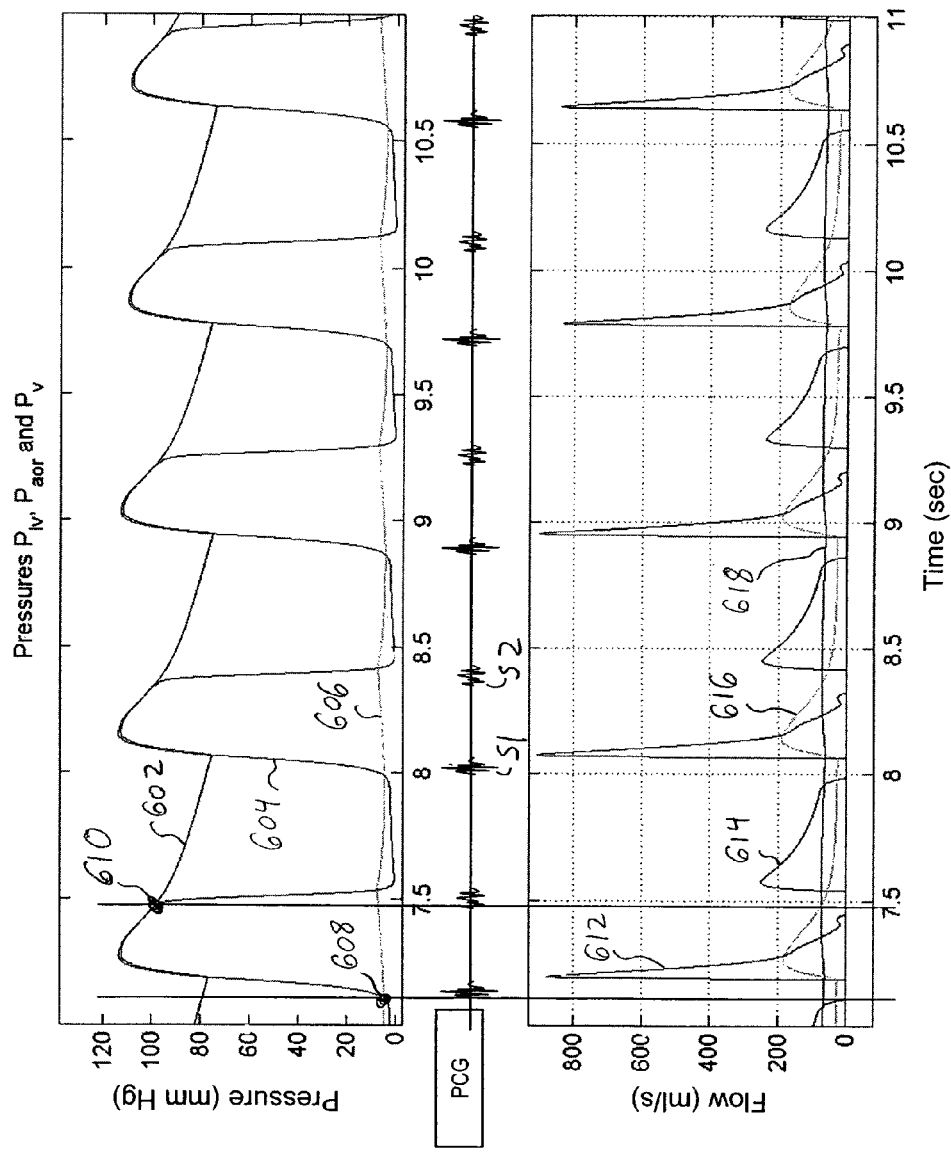
FIG. 6 is an example non-anomalous signal generated using the exemplary method shown in FIG. 5 according to an aspect of the present invention.

In step 502, an S1 onset time is determined according to where the LV pressure becomes greater than the venous pressure. FIG. 6 shows an example non-anomalous signal generated using an exemplary method of the present invention. S1. In FIG. 6, the LV pressure is illustrated as signal 604 and the venous pressure is illustrated as signal 606. Because the pressure signals, are cyclical, there are a plurality of onset times for locations where the LV pressure becomes greater than the venous pressure. One of the locations is illustrated by location 608. The onset time for each S1 over time can be similarly determined.

In step 504, an S2 onset time is determined according to where the LV pressure, signal 604, becomes less than the aortic pressure, illustrated by signal 602. Because the pressure signals are cyclical, there are a plurality of onset times for S2. One of the onset times is illustrated by location 610. The onset time for each S2 over time can be similarly determined.

In step 506, a predetermined S1 is inserted into predetermined signal 402 (FIG. 4) at the appropriate S1 onset times. In step 508, a predetermined S2 is inserted into predetermined signal 402 (FIG. 4) at the appropriate S2 onset times. The non-anomalous signal 412 (FIG. 4) is thus generated having S1 and S2 events, as shown by the PCG signal in FIG. 6.

In alternate step 510, the amplitude of the S1 and S2 may be adjusted. In an exemplary embodiment, time derivatives of the aortic and LV pressures are used to adjust the amplitude of the valve closing sounds, i.e. S1 and S2.

FIG. 6 also illustrates flow signals generated from the lumped-parameter circuit 200. Flow across the aortic valve is illustrated by signal 612, flow across the mitral valve is illustrated by signal 614, flow across the aortic portion by signal 616 and flow across the systemic portion by signal 618. The physiological effects on the pressure and flow signals and thus the generation of the PCG signal may be analyzed. The flow, as well as the pressure signals may be used to generate murmurs, as described below.

Figure 7:
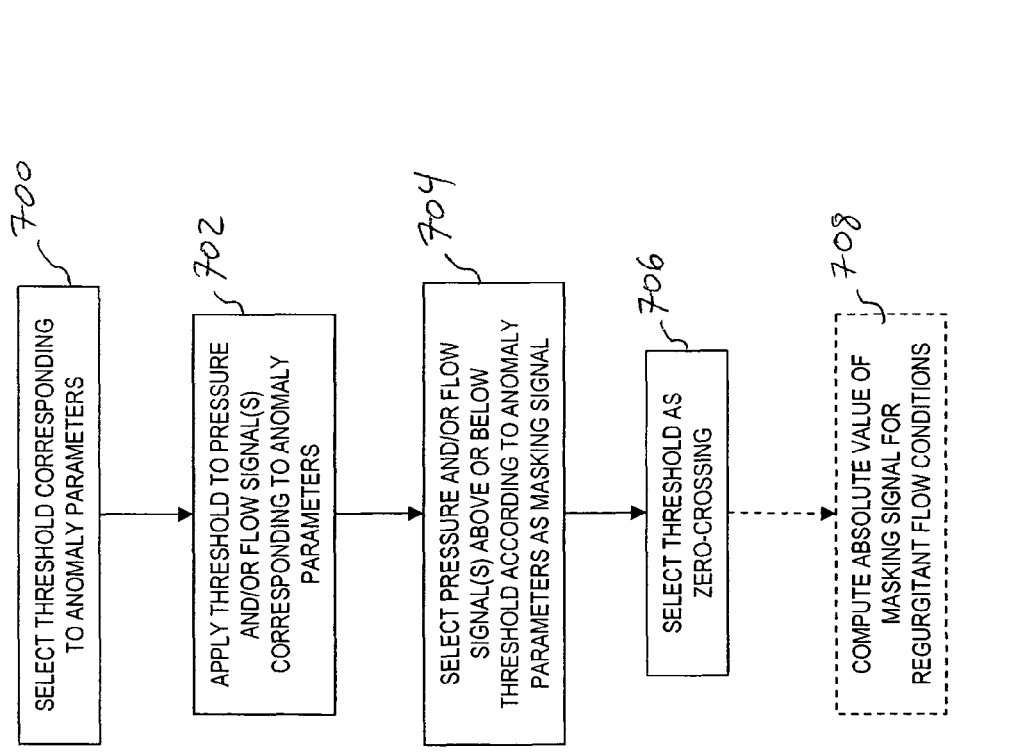
FIG. 7 is a flowchart illustrating an exemplary method for generating an anomalous signal according to an aspect of the present invention.

FIG. 7 shows a flowchart illustrating an exemplary method for generating an anomalous signal according to the present invention. Generation of a filtered noise signal 416 (FIG. 4) is described in above. FIG. 7 shows an exemplary method for generating timing and amplitude profile masking signal 418 (FIG. 4). In step 700, a threshold is selected corresponding to selected anomaly parameters.

In an exemplary embodiment, murmurs may be modeled by assuming that flow rates above the threshold may generate turbulence and thus a murmur. The Reynolds number, which is known as a measure to predict laminar or turbulent flow, may be defined as:

$$R = \rho dv/\eta \tag{7}$$

where $\rho$ is density, d is a diameter of a vessel, v is velocity and $\eta$ is viscosity. In the case of blood flow through a heart valve, it can be assumed that the density and the viscosity are relatively constant. Because the velocity is equal to flow divided by the cross-sectional area, the Reynolds number is proportional to flow, assuming that the diameter of the valve is relatively constant while open. Therefore, the flow can be considered a surrogate for the Reynolds number. Flow values above a threshold may represent turbulent flow. A threshold on the flow can thus represent the presence of a murmur.

A regurgitant flow can be generated under selected anomaly parameters. In general, the timing and magnitude for regurgitant flow can be determined based on a threshold. The flow below a threshold, i.e., the zero crossing may represent regurgitant flow. Although the regurgitant flow is described as the flow below a threshold, it is understood that regurgitant flow can also be considered to represent the magnitude of the flow above a threshold.

Figure 8:
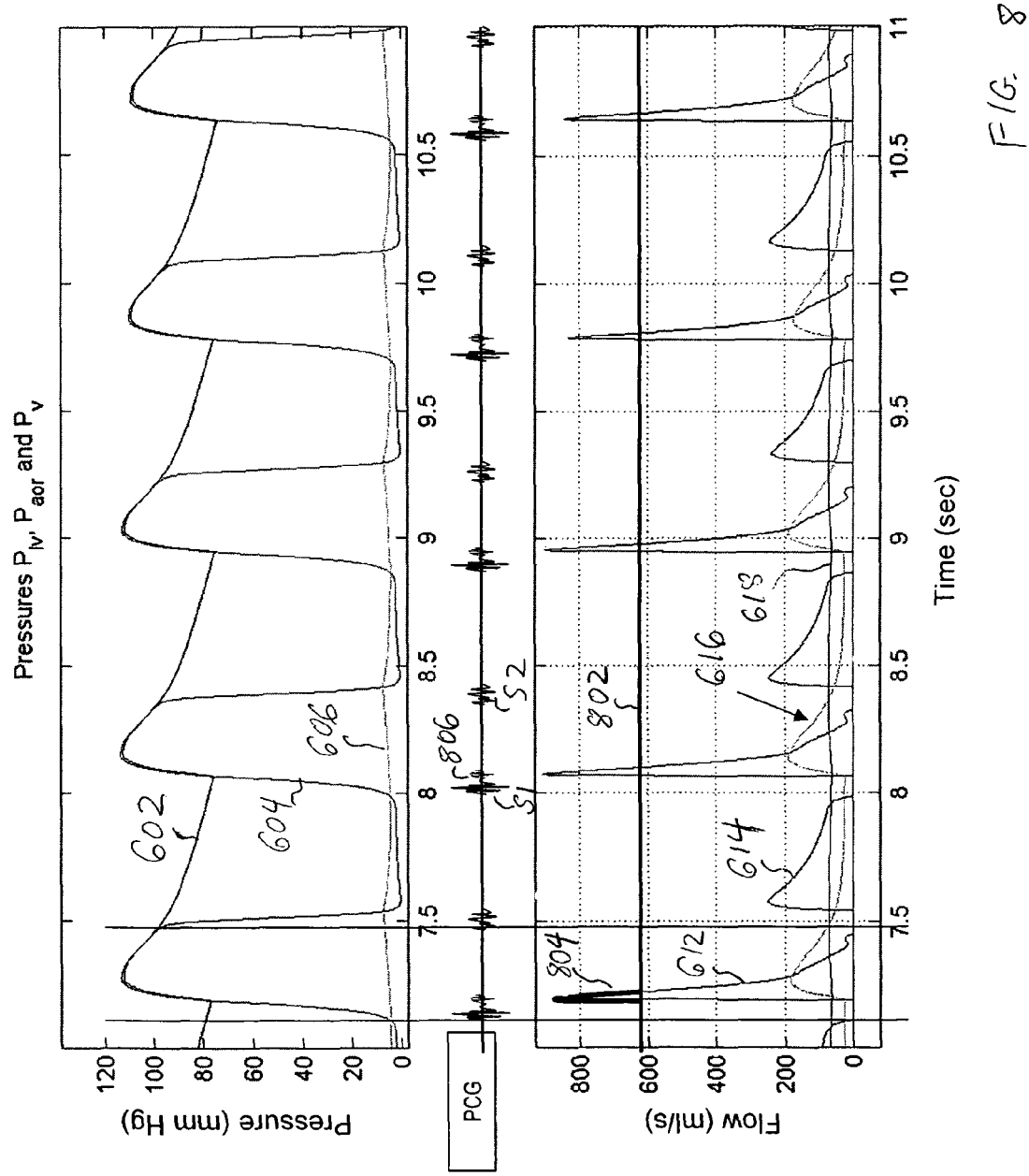
FIG. 8 is an example PCG signal including an anomalous signal generated using the method shown in FIG. 7 according to an aspect of the present invention.

In step 702, the selected threshold is applied to one or more pressure and/or flow signals according to the selected anomaly parameters. Signals chosen above a threshold may represent turbulent flow. Signals chosen below a threshold may represent regurgitant flow. FIG. 8 shows an example PCG signal including an anomalous signal generated using an exemplary method of the present invention. In FIG. 8, a threshold 802 is applied to flow through the aortic valve signal 612. The example shown in FIG. 8 represents generation of a functional ejection murmur.

In step 704, the portion of the signal above or below the threshold is selected as the masking signal. The shape of the flow function above or below the threshold may be used to provide an amplitude profile of the murmur. For example, portion 804 (FIG. 8) of the aortic valve flow signal 612 is selected for the masking signal. In step 706, the threshold, for example threshold 802 (FIG. 8) is selected as the zero crossing of the mask signal. The mask is used as the amplitude and timing profile for the generation of the murmur 806.

Figure 9:
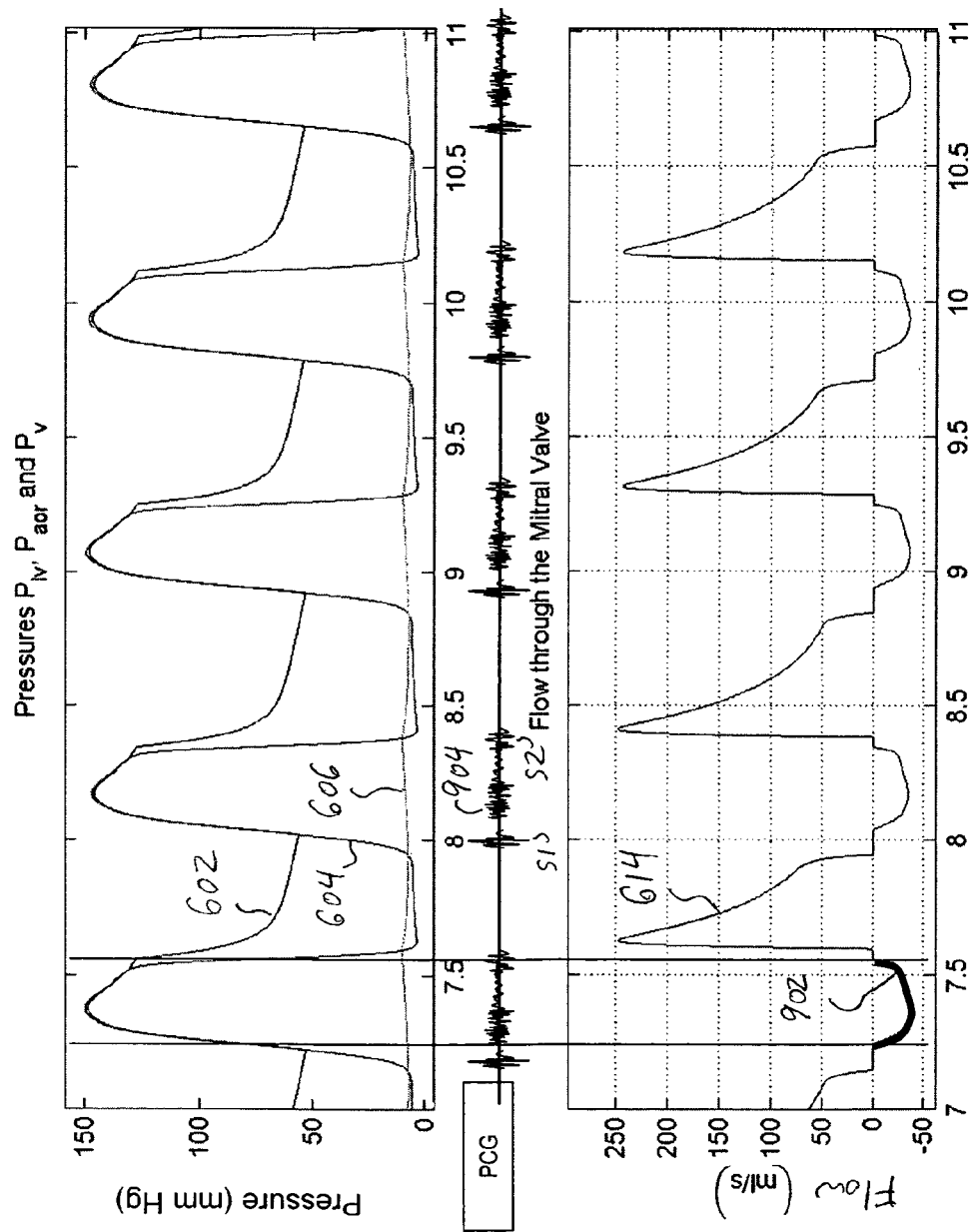
FIG. 9 is a further example PCG signal including an anomalous signal generated using the method shown in FIG. 7 according to an aspect of the present invention.

In alternate step 708, an absolute value of the masking signal is determined when the threshold is based upon anomaly parameters representing regurgitant flow. FIG. 9 shows a further example PCG signal including a further anomalous condition representing regurgitation generated using an exemplary method of the present invention. The example shown in FIG. 9 represents the generation of MR. In this condition, flow through the mitral valve signal 614 is used as the flow signal of interest. A threshold at the zero-crossing, step 700, is applied to mitral valve flow signal 614, step 702. The flow portion 902 below the threshold is selected as the masking signal, step 704. In this example, the threshold is at the zero-crossing, step 706. An absolute value of the masking signal is taken in step 708. The absolute value of the masking signal is used as an amplitude and timing profile for generation of the murmur 904.

Figure 10:
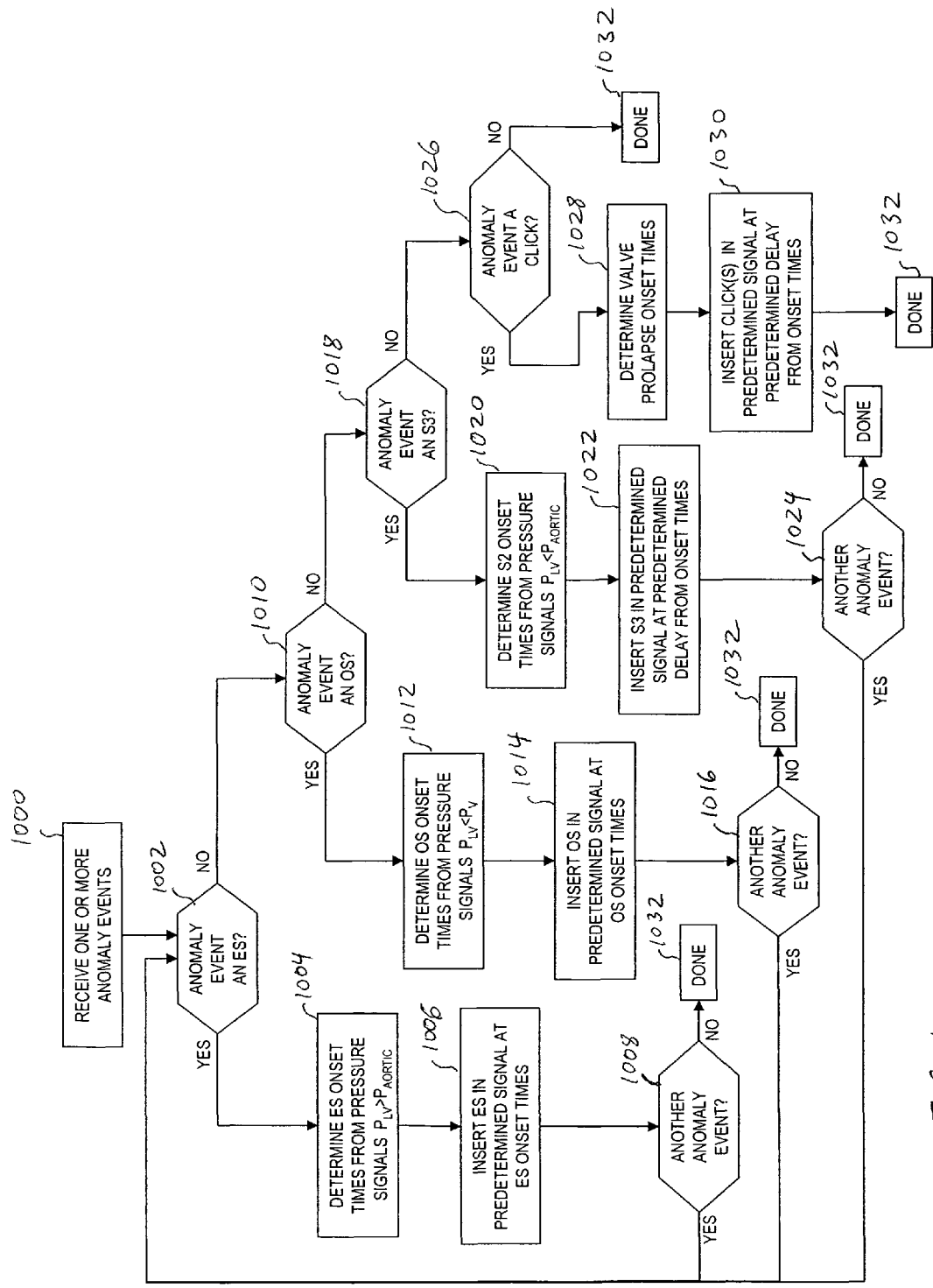
FIG. 10 is a flowchart illustrating an exemplary method for generating an anomalous signal consisting of anomaly events according to an aspect of the present invention.

FIG. 10 shows a flowchart illustrating an exemplary method for generating an anomalous signal consisting of anomaly events according to the present invention. In step 1000, one or more anomaly events are received, for example, based upon anomaly parameters selected by input parameter selector 102 (FIG. 1). In step 1002, a decision is made whether the received anomaly event includes an ES.

If the anomaly event includes an ejection sound (ES), processing proceeds to step 1004. In step 1004, ES onset times are determined from where the LV pressure, signal 604, becomes greater than the aortic pressure, signal 602 (FIG. 6). Because the pressure signals are cyclical, there are a plurality of onset times for ES events. In step 1006, a predetermined ES is inserted into a predetermined signal, for example signal 406 (FIG. 4), at the determined ES onset times. The predetermined ES may be retrieved, for example, from heart sounds database 116 (FIG. 1). In step 1008, a decision is made whether a further anomaly event has been received. If no other anomaly event is received, step 1008 proceeds to step 1032 and the process is complete. If another anomaly event is received, step 1008 proceeds to step 1002.

If the anomaly event does not include an ES, processing proceeds to step 1010. In step 1010, a decision is made whether the anomaly event includes an opening snap (OS).

If the anomaly event includes an OS, processing proceeds to step 1012. In step 1012, OS onset times are determined from where the LV pressure, signal 604, becomes less than the venous pressure 606 (FIG. 6). Because the pressure signals are cyclical, there are a plurality of onset times for OS events. In step 1014, a predetermined OS is inserted into a predetermined signal, for example signal 406 (FIG. 4), at the determined OS onset times. The predetermined OS may be retrieved, for example, from heart sounds database 116 (FIG. 1). In step 1016, a decision is made whether a further anomaly event has been received. If no other anomaly event is received, step 1016 proceeds to step 1032 and the process is complete. If another anomaly event is received, step 1016 proceeds to step 1002.

If the anomaly event does not include an OS, processing proceeds to step 1018. In step 1018, a decision is made whether the anomaly event includes an S3 event.

If the anomaly event includes an S3 event, processing proceeds to step 1020. In step 1020, S2 onset times are determined from where the LV pressure, signal 604, becomes less than the aortic pressure 602 (FIG. 6). Because the pressure signals are cyclical, there are a plurality of onset times for S2 events. Note that step 1020 is the same as step 504 (FIG. 5). In step 1022, a predetermined S3 event is inserted into a predetermined signal, for example signal 406 (FIG. 4), at a predetermined delay from the determined S2 onset times. Alternatively, the onset times may be determined from locations of maximum deceleration of the infilling of blood into the ventricle after the mitral valve opens. Peaks can thus be determined using an acceleration curve of blood flow in the mitral portion of circuit 200 to compute S3 onset times.

The predetermined S3 event may be retrieved, for example, from heart sounds database 116 (FIG. 1). In step 1024, a decision is made whether a further anomaly event has been received. If no other anomaly event is received, step 1024 proceeds to step 1032 and the process is complete. If another anomaly event is received, step 1024 proceeds to step 1002.

If the anomaly event does not include an S3 event, processing proceeds to step 1026. In step 1026, a decision is made whether the anomaly event includes a click. If the anomaly event does not include a click, processing proceeds to step 1032 and the process is complete.

If the anomaly event includes a click, processing proceeds to step 1028. In step 1028, valve prolapse onset times are determined. Because the pressure signals are cyclical, there are a plurality of valve prolapse onset time events. In step 1030, one or more predetermined clicks are inserted into a predetermined signal, for example signal 406 (FIG. 4). Whether one or more clicks are inserted may be a based on the selected anomaly parameters, for example selected by input parameter selector 102 (FIG. 1). The predetermined click may be retrieved, for example, from heart sounds database 116 (FIG. 1). Step 1030 proceeds to step 1032 and the processing is complete.

Figure 11:
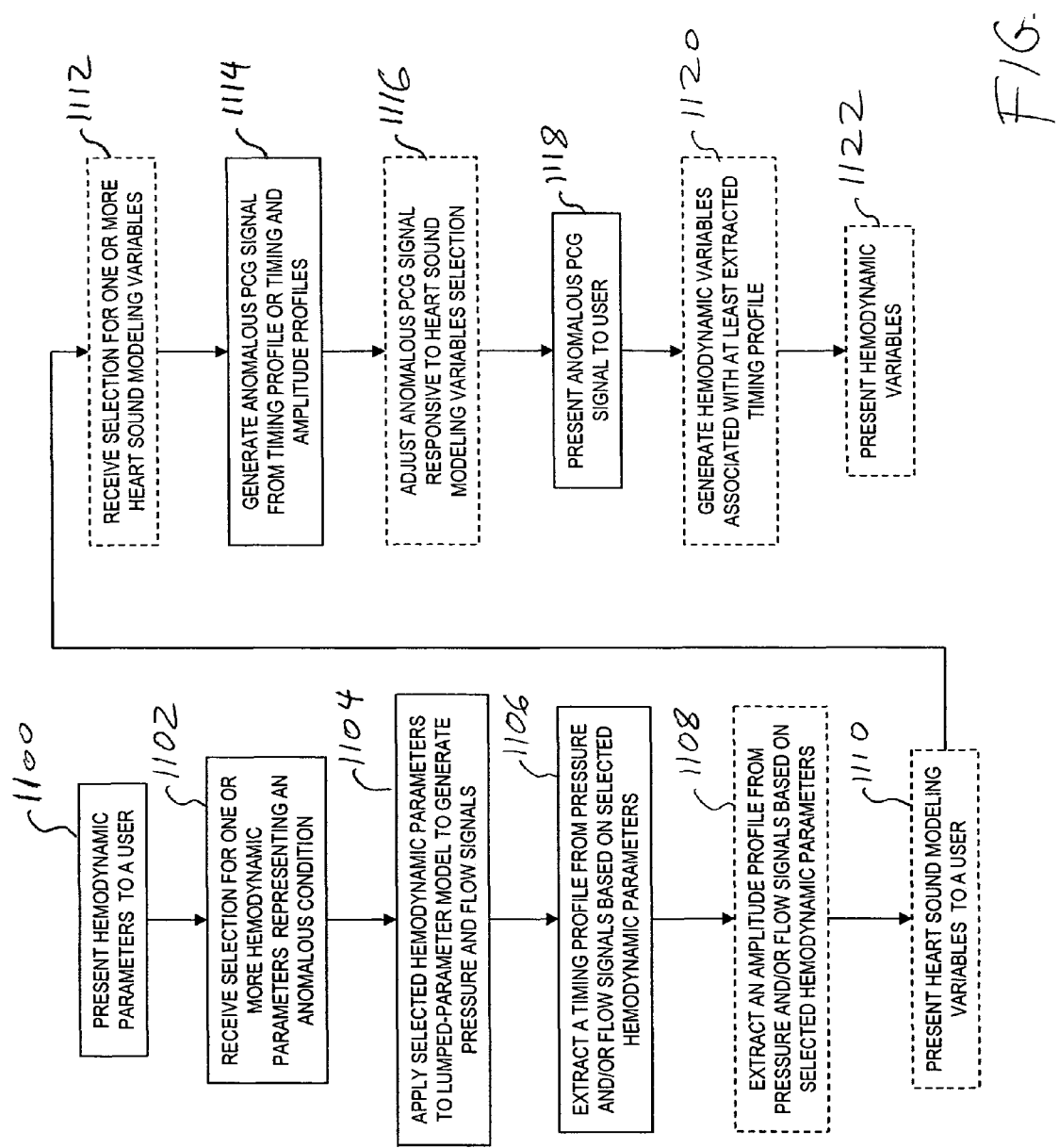
FIG. 11 is a flowchart illustrating an exemplary method for teaching auscultation according to an aspect of the present invention.

FIG. 11 shows a flowchart illustrating an exemplary method for teaching auscultation according to the present invention. In step 1100, hemodynamic parameters are presented to a user. The hemodynamic parameters may include one or more known parameters such as a constant heart rate, a variable heart rate, a respiration rate, a pathophysiology, a sinus arrhythmia parameter, an electrophysiology parameter, a premature ventricular beat parameter and a heart model selection parameter. It is contemplated that other hemodynamic parameters may be used within the scope of the present invention.

In step 1102, a selection is received from the user for one or more of the presented hemodynamic parameters. The selection may represent an anomalous condition. The anomalous condition may be associated, for example, with a functional murmur, a valvular pathology, systemic hypertension or a congenital anomaly. It is understood that a non-anomalous condition may also be selected, for example to examine the influence of respiration on the generated PCG signal.

In step 1104, the selected hemodynamic parameters are applied to a lumped-parameter heart model to generate pressure and flow signals, as described above. In step 1106, a timing profile is extracted from one or more pressure and/or flow signals based on the selected hemodynamic parameters. An exemplary timing profile extraction method is described above. In alternate step 1108, an amplitude profile is extracted from one or more pressure and/or flow signals based on the selected hemodynamic parameters. An amplitude profile may be extracted, for example, if the selected hemodynamic parameters indicate a murmur. An exemplary method for timing and amplitude profile extraction is described above.

In alternate step 1110, heart sound modeling variables may be presented to the user. The heart sound modeling variables may include one or more variables such as a murmur frequency characteristic selector, a murmur loudness, a murmur loudness grade, a background noise parameter, a respiration variability parameter and an auscultation site parameter. The auscultation site parameter desirably represents standard auscultation locations such as 2R, 2L, 4L and apex on the chest wall. In alternate step 1112, a selection is received for one or more of the presented heart sound modeling variables.

In step 1114, an anomalous PCG signal is generated using the extracted timing profile. The anomalous PCG signal may also be generated responsive to the extracted timing profile and amplitude profile. The anomalous PCG signal desirably includes at least S1 and S2 heart sounds, at a heart rate and arrhythmia parameter selected by the user. The anomalous PCG signal may further include at least one of a click, one or more types of murmurs, an ES, an OS, a third heart sound and a fourth heart sound. It is contemplated that the anomalous PCG signal may further include other sounds including non-heart sounds such as bowel sounds and/or background noise artifacts.

In alternate step 1116, the anomalous PCG signal may be adjusted responsive to the selected heart sound modeling parameters. In step 1118, the anomalous PCG signal is presented to a user, for example using graphical display 136 and audio output 138 (FIG. 1).

In alternate step 1120, exemplary hemodynamic variables are generated based on the extracted timing profile or the extracted timing profile and the extracted amplitude profile. The hemodynamic variables may further be determined based on the selected heart sound modeling parameters. For example, the hemodynamic variables may include one or more variables such as a stroke volume, an end-diastolic volume, a cardiac output, an ejection fraction, a systolic/diastolic blood pressure, a mean arterial pressure, an estimated mean arterial pressure, a systolic interval duration, and a diastolic interval duration. It is contemplated that other hemodynamic variables may further be computed as desired. In alternate step 1122, the generated hemodynamic variables may be presented.

FIG. 12 is an example display 1200, of exemplary system graphical display 136 shown in FIG. 1 that may be used with an embodiment of the present invention. Display 1200 desirably includes hemodynamic parameter selectors 1202 for selecting desired hemodynamic parameters to represent an anomalous condition. The hemodynamic parameter selectors 1202 may include a heart model selector, a heart rate selector, a respiration rate selector, a pathophysiology selector, an electrophysiology selector, a sinus arrhythmia selector, a premature ventricular beat (VPB) selector and a heart model display selector. It is understood that any selector representing a desired hemodynamic parameter may be included. A user may select one or more of the hemodynamic parameters to represent a desired anomalous condition. It is understood that parameters representing a non-anomalous condition, for example a sinus arrhythmia or a PCG at a constant selected heart rate, may also be selected.

Display 1200 may include a hemodynamic variable display 1204 for presenting hemodynamic variables computed according to the selected hemodynamic parameters from hemodynamic parameter selectors 1202. The hemodynamic variables may include a stroke volume (SV), an end-diastolic volume (EDV), a cardiac output (CO), an ejection fraction (EF), a systolic/diastolic blood pressure (BP), a mean arterial pressure (MAP), an estimated MAP, a systolic interval duration (Syst) and a diastolic interval duration (Diast). It is understood that any desired hemodynamic variables associated with the selected hemodynamic parameters may be computed and presented.

It is contemplated that a user may further adjust hemodynamic parameters using hemodynamic parameters selector 1202 to observe the effects of the adjusted hemodynamic parameters on the hemodynamic variables presented in hemodynamic variable display 1204. In this manner, a user may examine the throughput of blood by the heart and learn the physiological effects of various hemodynamic parameters including pathophysiology on the hemodynamic variables. A user may also adjust the hemodynamic parameters to obtain a desired hemodynamic variable, such as a systolic interval duration.

Display 1200 may include heart sound variable selectors 1206 for selecting amplitude parameters and frequency characteristic parameters in order to further adjust the synthesized anomalous PCG signal. Heart sound variable selectors 1206 may include a respiration variability selector, a background noise selector, a murmur loudness selector, a murmur frequency characteristic selector and an auscultation site selector. It is understood that the variables shown are exemplary, any desired heart sound variables may be included.

Display 1200 may include pressure graph 1208 and flow graph 1210 generated by a selected lumped-parameter heart model responsive to the hemodynamic parameter selectors 1202 and the heart sound variable selectors 1206. Pressure and flow graphs 1208 and 1210 are desirably time-aligned. It is contemplated that display 1200 may further include a display (not shown) of the selected lumped-parameter heart model used for computation. The lumped-parameter heart model may be displayed in place of pressure graph 1208, flow graph 1210, or the combination thereof or the lumped-parameter heart model may be presented as a separate display screen.

Pressure graph 1208 and flow graph 1210 may include one or more threshold adjustors such as threshold adjustor 1212, for manually adjusting a murmur threshold level used to generate the anomalous PCG signal. It is contemplated that multiple threshold adjustors may be presented with flow graph 1210 to adjust various thresholds associated with respective flow signals presented on the respective flow graph 1210. It is understood that although threshold adjustor 1212 is illustrated as adjusting a threshold associated with flow graph 1210, one or more threshold adjustors (not shown) may be similarly included with pressure graph 1208.

Display 1200 desirably includes a PCG signal indicator 1214 for displaying the synthesized anomalous PCG signal. PCG signal indicator 1214 may further present annotation of the PCG signal for different heart sounds such as S1, S2, S3, murmurs, clicks, ES and OS. Alternatively, PCG signal indicator 1214 may highlight the PCG signal such as with different colors to emphasize different heart sound events. It is desirable that PCG signal indicator 1214 display the PCG signal time-aligned with each of the pressure and flow graphs 1208 and 1210, respectively.

PCG signal indicator 1214 may allow for displaying a portion of the PCG, for example by highlighting a section of the PCG signal selected using a pointing device such as a mouse. It is desirable that a corresponding portion of pressure and flow graphs 1208 and 1210 be displayed with the selected portion of the PCG signal.

It is further contemplated that pressure and flow graphs 1208 and 1210 may include vertical bar indicators (not shown) which extend to an appropriate location on PCG signal indicator 1214 to illustrate a relationship between locations on pressure and flow signals displayed on pressure and flow graphs 1208 and 1210 and a PCG signal displayed in PCG signal indicator 1210. It is contemplated that the vertical indicators may be positioned automatically or may be positioned manually by a user. For example, a vertical indicator may be automatically placed at a location where the LV pressure becomes greater than the venous pressure and thus extend to the onset of an S1 event on PCG signal indicator 1214. It is contemplated that a user may adjust, add and remove vertical indicators as desired.

PCG signal indicator 1214 may include a playback indicator 1216 to provide audio review of the synthesized PCG signal. It is contemplated that playback indicator 1216 may, itself, include a selector for a slower audio playback suitably processed to maintain the same pitch frequency/content. PCG signal indicator 1214 may include a vertical bar for scrolling along the PCG signal or, alternatively, a change in signal highlighting to indicate a temporal location within the PCG signal during audio playback of the PCG signal.

PCG signal indicator 1214 may include a pressure-volume loop 1218 that represents pressure (vertical axis) and volume (horizontal axis) of each cardiac cycle (i.e. systole and diastole) over the generation of the PCG signal. Point A represents the start of systole, point B represents the opening of the aortic valve, point C represents the start of diastole and point D represents the opening of the mitral valve. Point E on pressure-volume loop 218 represents the initial conditions for the model. Pressure-volume loop 1218 may be responsive to a selected heart rate selected from among hemodynamic parameter selectors 1202.

The present invention is illustrated by reference to a number of examples. The examples are included to more clearly demonstrate the overall nature of the invention. These examples are exemplary, not restrictive of the invention.

Example of Mitral Regurgitation

There are numerous diverse causes of MR, including congenital conditions and disease processes and trauma affecting the valve cusps, valve seat and supporting structures such as the papillary muscle and chordae tendinae. The volume of regurgitated blood tends to raise the pressure in the left atrium, which stimulates atrial hypertrophy and causes rapid ventricular filling in early diastole. Systemic arterial hypertension typically exaggerates MR.

As described above, the auscultatory features of MR include a dull or absent S1, a holosystolic murmur, a split S2, an exaggerated third heart sound (S3) and a short mid-diastolic rumble. The holosystolic murmur is produced by the backward flow of blood through the partially open mitral valve. For this reason, the murmur can extend through S2 up to the point of mitral closure in early diastole. For a partially competent MV, the valve may begin to regurgitate after the transvalvular reverse pressure exceeds a certain threshold, such that the systolic murmur resulting from regurgitant flow may begin later in systole. The amplitude profile of the murmur is variable. For severe MR, for example, it is generally a plateau. The sound quality of the murmur may be described as blowing or musical and is typically not of a harsh quality. A musical murmur is likely to be present, for example, during rheumatic carditis/endocarditis.

The musicality of the murmur may be represented by a single harmonic at a relatively high frequency of about 800 Hz on top of a broadband murmur. Example spectra of blowing systolic MR murmurs may be used to estimate a bandwidth of about 60-300 Hz, ranging as high as 400-600 Hz.

Referring back to FIG. 9, anomaly parameters are described for generating the illustrated MR condition according to an embodiment of the present invention. MR can be modeled by decreasing the backward resistance of the mitral valve diode 204 (FIG. 2A). The holosystolic murmur may be modeled by applying a threshold to the reverse flow through the mitral valve, i.e. the zero crossing, and the flow below this threshold, 902, can be used to generate the amplitude profile of the systolic murmur, as described above. The systolic murmur may be modeled using bandpass filtered white noise and may further include an overtone according to the type of murmur quality desired. FIG. 9 illustrates modeling of the systolic murmur. The effects on S1, S2, S3 and a diastolic rumble are not shown but may be modeled according to an exemplary method described herein.

A frequency characteristic of the blowing murmur may be simulated with a bandpass filter that passes about 60-300 Hz. A frequency characteristic of the broadband murmur may be simulated with a bandpass filter that passes about the 60-500 Hz. A frequency characteristic of the musical and blowing murmur may be simulated by combining the output of a bandpass filter that passes about 60-300 Hz and an about 800 Hz overtone.

Example of Mitral Valve Prolapse

The basic pathology of mitral valve prolapse (MVP) is a degeneration of the mitral valve, resulting in a floppy valve which billows into the left atrium. The auscultatory findings of MVP are typically variable. Some heart beats may have only a click or multiple clicks, while other heart beats may have a late systolic murmur or a combination of a click and a murmur. The murmur has been described as a musical whoop or honk. The findings may be transient and intermittent. Sometimes the findings are heard on inspiration only while at other times they are heard on expiration. The clicks are typically high frequency sounds best heard at the apex location. The click may be produced by the halting of the prolapsing posterior cusp. The timing of the click typically varies with posture such that it is heard earlier in the upright posture than in the reclining posture.

According to modeling consideration, a prolapse occurs after a peak pressure has been exceeded. A transvalvular pressure threshold may be set such that when the reverse pressure threshold is exceeded, the valve prolapse can be modeled. According to the present example, a prolapse occurs if the difference between the LV pressure and the venous pressure is greater than a predetermined threshold. The valve prolapse can then be modeled by reducing the back resistance of the mitral valve diode 204 (FIG. 2A) to allow for regurgitant flow.

The regurgitant flow may or may not generate a murmur. A flow threshold can be applied to the regurgitant flow to determine the existence and amplitude profile of the regurgitant murmur. A murmur may not tail off until early diastole or until the mitral valve closes, as long as the prolapsed valve permits regurgitant flow. A frequency characteristic of the regurgitant murmur may be modeled using a bandpass filter that passes about 20 Hz to 200 Hz.

Clicks can be associated with a prolapse event. At a delay after the valve prolapses, its motion may halt abruptly thus causing one or more clicks. One or more clicks can thus be inserted after the onset of the regurgitant flow murmur.

Figure 13:
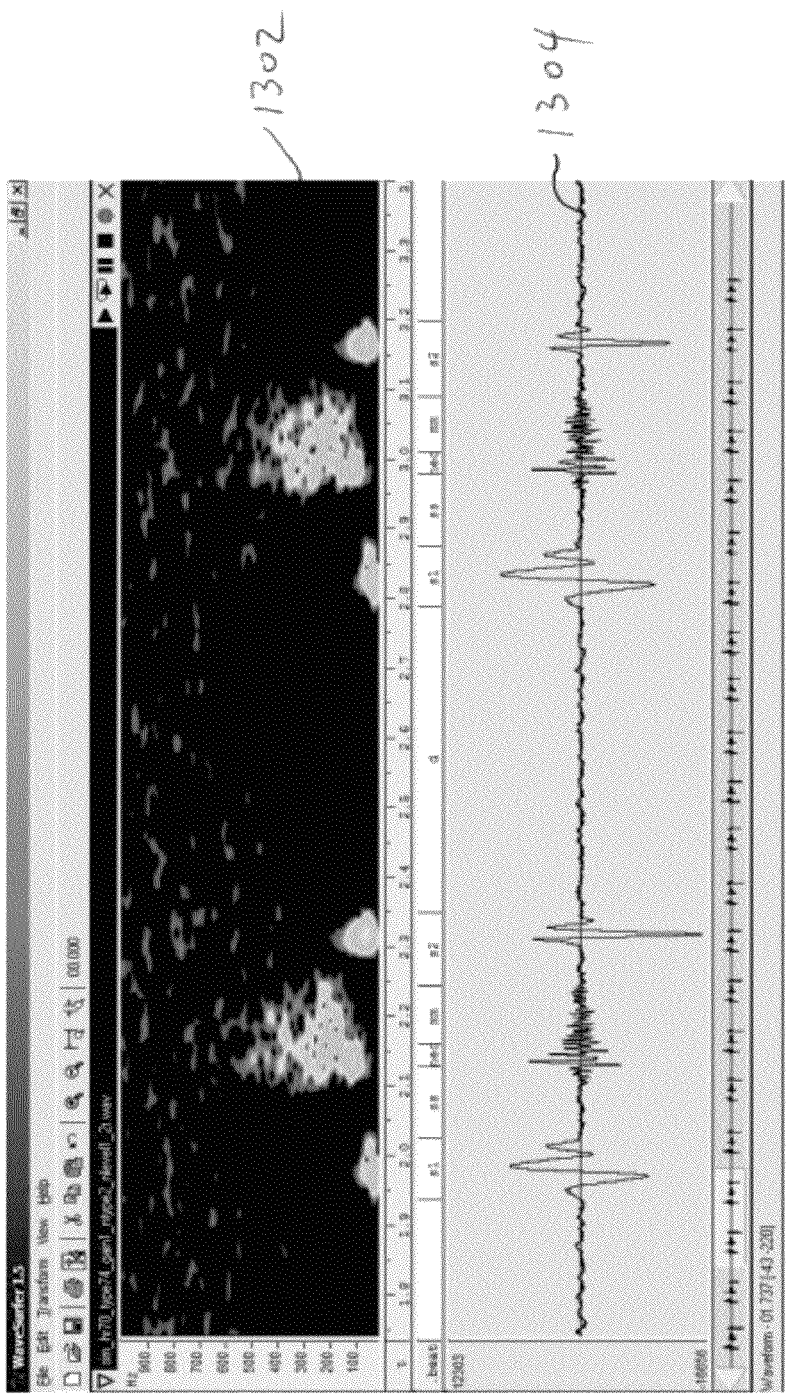
FIG. 13 illustrates an example generated mitral valve prolapse condition according to an embodiment of the present invention.

FIG. 13 illustrates an example mitral valve prolapse condition generated according to an embodiment of the present invention. A single click and a regurgitant murmur are modeled according to the above description to generate one typical set of of MVP auscultatory findings. A spectrogram 1302 of the MVP condition, as well as an annotated PCG signal 1304 including S1, S2, click and murmur annotation illustrates the timing and frequency of the various heart sound events.

Example of Mitral Stenosis

Rheumatic fever is typically the cause of mitral stenosis (MS). Rheumatic fever may cause the mitral cusps to become partially fused together. The mitral cusps may also become thickened by a fibrosing process. Mitral orifices that are stenosed may have a cross sectional area less than or equal to 1 cm$^2$ whereas the normal cross-sectional area is typically on the order of 5 cm$^2$. Mild symptoms may be determined when the valve aperture becomes 3 cm$^2$.

The auscultatory findings typically include a regurgitant systolic murmur, an OS, and a diastolic murmur. The S1 and S2 heart sounds are also typically affected. The first heart sound may be delayed due to increased left atrial (venous) pressure such that systole is typically short. A systolic murmur may occur if there is significant regurgitation. The timing of the OS is a function of the left atrial (venous) pressure. In severe MS, the S2-OS interval may be 50 msec, whereas for mild MS, this interval may be up to 140 msec. A diastolic murmur, having a rumbling quality, typically begins after the OS. Published spectrograms of MS show a broadband murmur from about a very low frequency, near 0 Hz, to 120 Hz, sometimes as high as 200 Hz.

MS may be modeled by increasing the forward resistance of mitral valve diode 204 (FIG. 2A). A decrease in the cross-sectional area can be reflected by an increase of flow resistance by a factor of about 25. A mild decrease in cross-sectional area by about 1.7 may result in an estimated increase in resistance by a factor of about 2.8. A threshold may thus be applied to the flow through the mitral valve portion according to the severity of MS, as described above.

Figure 14:
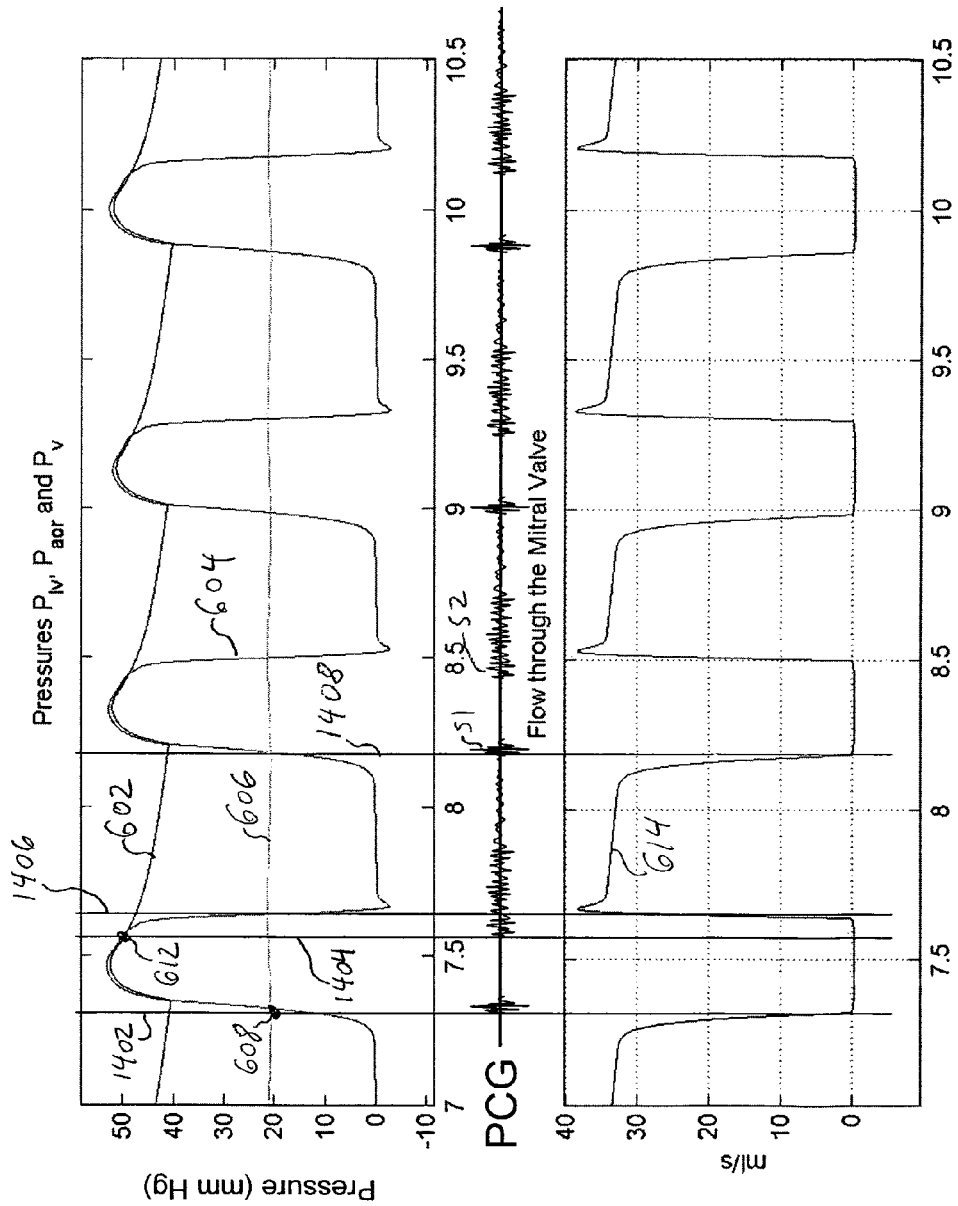
FIG. 14 illustrates an example generated mitral stenosis condition according to an embodiment of the present invention.

FIG. 14 illustrates an example generated MS condition according to an embodiment of the present invention. Vertical line 1402 illustrates the onset of S1, i.e. at location 608. Vertical line 1404 illustrates the onset of S2, i.e. at location 612. Vertical line 1406 illustrates the onset of the diastolic murmur. Vertical line 1408 illustrates the onset of the next S1 and also the end of the diastolic murmur. The murmur timing and amplitude profile may be obtained by applying a threshold between vertical lines 1406 and 1408 where flow through mitral valve signal 614 intersects the vertical lines to generate the masking signal as described above. The frequency characteristics of the diastolic murmur may be synthesized using a bandpass filter that passes about 10-120 Hz to simulate a low rumbling murmur. Alternatively, a bandpass filter that passes 20 Hz-200 Hz may be used to simulate a medium rumbling murmur. FIG. 14 shows that the filling volume is reduced as compared to a non-anomalous condition, such as shown in FIG. 6. The systolic interval is also shortened as compared to a non-anomalous condition. FIG. 14 does not illustrate the systolic murmur or the OS. It is understood that these events may be generated according to the exemplary method described herein.

Although the invention has been described as apparatus and a method, it is contemplated that it may be practiced by a computer configured to perform the method or by computer program instructions embodied in a computer-readable carrier such as an integrated circuit, a memory card, a magnetic or optical disk or an audio-frequency, radio-frequency or optical carrier wave.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method for simulating a phonocardiogram (PCG) signal including an anomalous condition, the method comprising the steps of:
   providing a lumped-parameter heart model responsive to anomaly parameters representing the anomalous condition;
   generating pressure and flow signals from the heart model;
   extracting a timing profile or the timing profile and an amplitude profile associated with the anomalous condition from at least one of the generated pressure and flow signals;
   generating an anomalous signal using the anomaly parameters and the extracted timing profile or the extracted timing profile and the extracted amplitude profile; and time-aligning and combining a non-anomalous signal and the generated anomalous signal to form a combined signal, the combined signal representing the PCG signal.

2. The method according to claim 1, wherein the anomaly parameters are determined from input parameters, the input parameters including at least one of a constant heart rate, a variable heart rate, a respiration rate, a pathophysiology, a sinus arrhythmia parameter, an electrophysiology parameter or a premature ventricular beat parameter.

3. The method according to claim 1, wherein the anomalous signal is represented by one or more of a click, a murmur, an ejection sound, an opening snap, a third heart sound or a fourth heart sound.

4. The method according to claim 1, wherein the anomalous condition is associated with at least one of a functional murmur, a valvular pathology, systemic hypertension or a congenital anomaly.

5. The method according to claim 1, wherein the anomaly parameters include a predetermined respiratory cycle and a variable heart rate, and the step of generating the pressure and flow signals includes providing the respiratory cycle and the variable heart rate to the lumped-parameter heart model,
wherein the predetermined respiratory cycle and the variable heart rate cause the generation of pressure and flow signals associated with a sinus arrhythmia.

6. The method according to claim 1, wherein the step of time-aligning and combining the non-anomalous signal and the generated anomalous signal further includes the step of adjusting the amplitude of the combined signal responsive to a predetermined respiratory cycle.

7. The method according to claim 1, wherein the non-anomalous signal is stored in a database and the method includes selecting the stored non-anomalous signal associated with anomaly parameters.

8. The method according to claim 1, the method further comprising the steps of:
receiving one or more further anomaly parameters; and
the step of generating the anomalous signal further includes generating the anomalous signal responsive to the received one or more further anomaly parameters,
wherein the further anomaly parameters include an anomaly frequency characteristic and an anomaly loudness parameter.

9. The method according to claim 1, the method further including the steps of:
receiving one or more heart sound parameters; and
the step of time aligning and combining the non-anomalous signal and the generated anomalous signal further includes processing the combined signal responsive to the received one or more heart sound parameters,
wherein the one or more heart sound parameters include a background noise level, an auscultation site and a respiration variability.

10. The method according to claim 1, wherein the generated pressure signals include a left ventricular (LV) pressure signal, a venous pressure signal and an aortic pressure signal, the method including the steps of:
determining a first onset time associated with the LV pressure signal being greater than the venous pressure signal, the first onset time being associated with a first heart sound;
determining a second onset time associated with the LV pressure signal being less than the aortic pressure signal, the second onset time being associated with a second heart sound;
inserting a predetermined first heart sound into a further predetermined signal at the first onset time; and
inserting a predetermined second heart sound into the further predetermined signal at the second onset time, the predetermined signal including the inserted predetermined first heart sound and the inserted predetermined second heart sound representing the non-anomalous signal.

11. The method according to claim 10 the method further including the step of adjusting an amplitude of each of the first heart sound and the second heart sound of the non-anomalous signal responsive to time derivatives of the generated pressure signals.

12. The method according to claim 1, wherein the generated pressure signals include a left ventricular (LV) pressure signal, a venous pressure signal and an aortic pressure signal, and the step of generating the anomalous signal includes the steps of:
determining an onset time of an anomalous event according to a pressure condition between the generated pressure signals; and
inserting a predetermined anomalous event into a predetermined signal at the determined onset time, a length of the predetermined signal corresponding to the non-anomalous signal,
wherein:
the anomalous event includes at least one of a click, a third heart sound, a fourth heart sound, an opening snap or an ejection sound,
the pressure condition is associated with the LV pressure being less than the venous pressure when the anomalous event includes the opening snap,
the pressure condition is associated with a pressure difference between the LV pressure and the venous pressure being greater than a predetermined threshold and the onset timing including a predetermined delay from the pressure condition when the anomalous event includes a click;
the pressure condition is associated with the LV pressure being greater than the aortic pressure when the anomalous event includes the ejection sound, and
the pressure condition is associated the LV pressure being less than the aortic pressure and the onset timing including a predetermined delay from the pressure condition when the anomalous event includes the ejection sound.

13. The method according to claim 1, the step of generating anomalous signal including:
generating a filtered noise signal by applying a noise signal to a filter characteristic associated with the anomaly parameters, the filtered noise signal having a length corresponding to the non-anomalous signal;
applying a threshold to at least one of one or more of the flow signals and one or more of the pressure signals to generate a masking signal, the masking signal corresponding to the extracted timing profile and the extracted amplitude profile; and
combining the masking signal and the generated filtered noise signal to form the anomalous signal.

14. The method according to claim 13, the step of generating the anomalous signal further including the steps of:
determining an onset time of an anomalous event according to a pressure condition between the generated pressure signals;

inserting a predetermined anomalous event into a predetermined signal at the determined onset time, a length of the predetermined signal corresponding to the non-anomalous signal to form an anomalous event signal; and combining the anomalous signal and the anomalous event signal, wherein the anomalous event includes at least one of a click, a third heart sound, a fourth heart sound, an opening snap or an ejection sound.

15. The method of claim 1, wherein the non-anomalous signal is a predetermined non-anomalous signal.

16. A non-transitory computer readable medium including a computer program that causes a computer to perform the method according to claim 1.

* * * * *

UNITED STATES PATENT AND TRADEMARK OFFICE
CERTIFICATE OF CORRECTION

PATENT NO. : 8,364,249 B2
APPLICATION NO. : 11/502900
DATED : January 29, 2013
INVENTOR(S) : Raymond Langworthy Watrous It is certified that error appears in the above-identified patent and that said Letters Patent is hereby corrected as shown below:

Drawings
In the drawings, Sheet 5, Fig. 3, Reference Numeral 318, delete "FRQUENCY"
and insert -- FREQUENCY --, therefor.

In the Specification
Column 6
Line 4, Delete "ore" and insert -- or --, therefor.

Column 7
Line 50, Delete "204," and insert -- 204' --, therefor.

Column 8
Line 9, Delete "52" and insert -- S2 --, therefor.

Column 10
Line 62, Delete "S" and insert -- S1 --, therefor.

Column 11
Line 30, Delete "heart beat." and insert -- heartbeat. --, therefor.

Column 12
Line 38, Delete "invention. S1." and insert -- invention S1. --, therefor.

Column 19
Line 10, Delete "heart beats" and insert -- heartbeats --, therefor.
Line 11, Delete "heart beats" and insert -- heartbeats --, therefor.
Line 48, Before "MVP" delete "of".

Signed and Sealed this
Twelfth Day of November, 2013

Teresa Stanek Rea
*Deputy Director of the United States Patent and Trademark Office*